US010842572B1

United States Patent
Viswanathan

(10) Patent No.: US 10,842,572 B1
(45) Date of Patent: Nov. 24, 2020

(54) METHODS, SYSTEMS, AND APPARATUSES FOR TRACKING ABLATION DEVICES AND GENERATING LESION LINES

(71) Applicant: Farapulse, Inc., Menlo Park, CA (US)

(72) Inventor: Raju Viswanathan, Mountain View, CA (US)

(73) Assignee: Farapulse, Inc., Menlo Park, CA (US)

( * ) Notice: Subject to any disclaimer, the term of this patent is extended or adjusted under 35 U.S.C. 154(b) by 0 days.

(21) Appl. No.: 16/785,392

(22) Filed: Feb. 7, 2020

Related U.S. Application Data

(60) Provisional application No. 62/940,219, filed on Nov. 25, 2019.

(51) Int. Cl.
*A61B 18/14* (2006.01)
*A61B 18/12* (2006.01)
(Continued)

(52) U.S. Cl.
CPC .......... *A61B 34/20* (2016.02); *A61B 18/1206* (2013.01); *A61B 18/1492* (2013.01); *A61B 34/10* (2016.02); *A61B 90/36* (2016.02); *A61B 2018/00577* (2013.01); *A61B 2018/00738* (2013.01); *A61B 2034/102* (2016.02);
(Continued)

(58) Field of Classification Search
CPC ........ A61B 2034/102; A61B 2034/104; A61B 2034/107; A61B 34/20; A61B 34/10; A61B 18/1206; A61B 18/1492; A61B 90/36; A61B 2018/00577; A61B 2034/2074; A61B 2090/367; A61B 2018/00738
See application file for complete search history.

(56) References Cited

U.S. PATENT DOCUMENTS 4,200,104 A 4/1980 Harris
4,438,766 A 3/1984 Bowers
(Continued)

FOREIGN PATENT DOCUMENTS

CN 105283143 A 1/2016
EP 1042990 A1 10/2000
(Continued)

OTHER PUBLICATIONS

Extended European Search Report for European Application No. 16884132.8, dated Jul. 8, 2019, 7 pages.
(Continued)

*Primary Examiner* — Jaymi E Della
*Assistant Examiner* — Sean W Collins
(74) *Attorney, Agent, or Firm* — Cooley LLP

(57) ABSTRACT

Systems, devices, and methods for electroporation ablation therapy are disclosed. An apparatus may be configured to activate a field generator to generate an electric or magnetic field such that signals are received by a receiver coupled to an ablation device disposed adjacent to a tissue surface. Processed data associated with the signals may be obtained. A position and an orientation of the ablation device may be determined based on the processed data. An expected ablation zone of the ablation device in the tissue surface may be determined based on the position and the orientation of the ablation device. A map of the tissue surface and a visual representation of the expected ablation zone disposed in the map of the tissue surface may be displayed.

26 Claims, 15 Drawing Sheets

(51) Int. Cl.
*A61B 34/20* (2016.01)
*A61B 34/10* (2016.01)
*A61B 90/00* (2016.01)
*A61B 18/00* (2006.01)

(52) U.S. Cl.
CPC . *A61B 2034/107* (2016.02); *A61B 2034/2074* (2016.02); *A61B 2090/367* (2016.02)

(56) References Cited

U.S. PATENT DOCUMENTS

| | | |
|---|---|---|
| 4,470,407 A | 9/1984 | Hussein |
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,558,091 A | 9/1996 | Acker et al. |
| 5,578,040 A | 11/1996 | Smith |
| 5,617,854 A | 4/1997 | Munsif |
| 5,624,430 A | 4/1997 | Eton et al. |
| 5,662,108 A | 9/1997 | Budd et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/200 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |

(56) References Cited

U.S. PATENT DOCUMENTS

| | | |
|---|---|---|
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harley et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harley et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,788,885 B2 | 10/2017 | Long et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,701 B2 | 11/2018 | Davalos et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |

(56) References Cited

U.S. PATENT DOCUMENTS

| | | |
|---|---|---|
| 10,322,286 B2 | 6/2019 | Viswanathan et al. |
| 10,342,598 B2 | 7/2019 | Long et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,531,914 B2 | 1/2020 | Stewart et al. |
| 10,625,080 B1 | 4/2020 | Viswanathan |
| 10,688,305 B1 | 6/2020 | Viswanathan |
| 10,709,502 B2 | 7/2020 | Viswanathan |
| 10,709,891 B2 | 7/2020 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0078494 A1* | 4/2003 | Panescu ............... A61B 8/4254 600/424 |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0147920 A1* | 7/2004 | Keidar ................. A61B 5/062 606/34 |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0134273 A1 | 6/2010 | Weiss et al. |
| 2010/0135550 A1* | 6/2010 | Arnon .................... A61B 5/015 382/128 |
| 2010/0137861 A1 | 6/2010 | Soroff et al. |
| 2010/0168550 A1* | 7/2010 | Byrd .................. A61B 5/1076 600/407 |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0015628 A1* | 1/2011 | Dalal ................. A61B 18/1477 606/34 |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |

(56) References Cited

U.S. PATENT DOCUMENTS

| | | |
|---|---|---|
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0109242 A1 | 5/2012 | Levin et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harley et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0080693 A1* | 3/2015 | Solis ............... A61B 5/0422 600/374 |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0223902 A1* | 8/2015 | Walker ............... A61B 34/20 600/424 |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |

(56) References Cited

U.S. PATENT DOCUMENTS

| | | |
|---|---|---|
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0078170 A1* | 3/2018 | Panescu ................ A61B 5/061 |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0145595 A1 | 5/2018 | Fontana et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0214195 A1 | 8/2018 | Fraasch et al. |
| 2018/0214202 A1 | 8/2018 | Howard et al. |
| 2018/0221078 A1 | 8/2018 | Howard et al. |
| 2018/0243558 A1 | 8/2018 | Athos et al. |
| 2018/0250508 A1 | 9/2018 | Howard |
| 2018/0289417 A1 | 10/2018 | Schweitzer et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0060632 A1 | 2/2019 | Asirvatham et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0192223 A1 | 6/2019 | Rankin |
| 2019/0201089 A1 | 7/2019 | Waldstreicher et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0231425 A1 | 8/2019 | Waldstreicher et al. |
| 2019/0233809 A1 | 8/2019 | Neal, II et al. |
| 2019/0256839 A1 | 8/2019 | Neal, II et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0376055 A1 | 12/2019 | Davalos et al. |
| 2020/0129233 A1 | 4/2020 | Viswanathan et al. |
| 2020/0139114 A1 | 5/2020 | Viswanathan et al. |
| 2020/0230403 A1 | 7/2020 | Bowers |

FOREIGN PATENT DOCUMENTS

| | | |
|---|---|---|
| EP | 1125549 | 8/2001 |
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |

(56) References Cited

FOREIGN PATENT DOCUMENTS

| | | |
|---|---|---|
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2018/208795 | 11/2018 |
| WO | WO 2019/118436 | 6/2019 |
| WO | WO 2019/133606 | 7/2019 |
| WO | WO 2019/133608 | 7/2019 |
| WO | WO 2019/147832 | 8/2019 |
| WO | WO 2019/152986 | 8/2019 |
| WO | WO 2019/173309 | 9/2019 |

OTHER PUBLICATIONS

Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 16/416,677, dated Aug. 15, 2019, 8 pages.
Office Action for U.S. Appl. No. 16/722,650, dated Mar. 25, 2020, 12 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
International Search Report and Written Opinion for International Application No. PCT/US2019/017322, dated May 10, 2019, 15 pages.
International Search Report and Written Opinion for International Application No. PCT/US2019/030922, dated Sep. 6, 2019, 12 pages.
Office Action for U.S. Appl. No. 16/573,704, dated Dec. 17, 2019, 6 pages.
Office Action for U.S. Appl. No. 16/741,506, dated Feb. 28, 2020, 5 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
Office Action for U.S. Appl. No. 16/723,407, dated Mar. 19, 2020, 13 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Tekle, E. et al., "Electroporation by using bipolar oscillating electric field: An improved method for DNA transfection of NIH 3T3 cells," Proc. Natl. Acad. Sci. USA, vol. 88, pp. 4230-4234, May 1991.
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
First Office Action for Chinese Application No. 201680077941.2, dated Jun. 30, 2020, 13 pages.
Office Action for U.S. Appl. No. 16/689,967, dated Jul. 22, 2020, 23 pages.
Notice of Reasons for Rejection for Japanese Application No. 2018-534869, dated Jul. 29, 2020, 11 pages.

* cited by examiner

METHODS, SYSTEMS, AND APPARATUSES FOR TRACKING ABLATION DEVICES AND GENERATING LESION LINES

CROSS REFERENCE TO RELATED APPLICATIONS

This application claims the benefit of U.S. Provisional Application No. 62/940,219, filed on Nov. 25, 2019, the entire disclosure of which is incorporated herein by reference in its entirety.

TECHNICAL FIELD

The embodiments described herein relate generally to medical devices for therapeutic electrical energy delivery, and more particularly to systems, apparatuses, and methods for tracking ablation devices (e.g., ablation catheters) and generating lesion lines using such devices.

BACKGROUND

Pulsed field ablation using application of high voltage pulses has been demonstrated to be suitable for the rapid and effective generation of lesions in cardiac tissue as well as other target anatomy. In the cardiac context, pulsed field ablation has been used for focal ablation or the generation of discrete local lesions. For example, an ablation catheter configured for focal ablation can be used to delivered pulsed field ablation via irreversible electroporation to cardiac tissue.

In a clinical catheter laboratory, electroanatomical mapping systems that use impedance tracking or impedance-based localization systems can be used to provide three-dimensional visualization feedback of devices positioned in patient anatomy. Additionally or alternatively, electromagnetic tracking sensors can be integrated into devices and used to track those devices within patient anatomy.

It can be desirable during an ablation procedure to track properties of an ablation device and use such information to assess ablation characteristics, e.g., to assist with ablation procedure planning.

SUMMARY

Described herein are systems, devices, and methods for visualizing and generating focal tissue ablation using an ablation catheter. In some embodiments, the ablation devices used in these systems may be deployed epicardially or endocardially in cardiac applications.

In some embodiments, an apparatus may include a memory; and a processor operatively coupled to the memory, the processor configured to: activate a field generator to generate an electric or magnetic field such that signals are received by a receiver coupled to an ablation device disposed adjacent to a tissue surface; obtain processed data associated with the signals; determine a position and an orientation of the ablation device based on the processed data; determine an expected ablation zone of the ablation device in the tissue surface based on the position and the orientation of the ablation device; and display, via an output device, a map of the tissue surface and a visual representation of the expected ablation zone in the map of the tissue surface.

In some embodiments, a method may include receiving, at a processor, data representative of signals received by a receiver coupled to an ablation device disposed adjacent to a tissue surface, the receiver receiving the signals in response to an electric or magnetic field being generated by a field generator; determining, at the processor, a position and an orientation of the ablation device based on the data representative of the signals; determining, at the processor, an expected ablation zone of the ablation device in the tissue surface based on the position and the orientation of the ablation device; and displaying, via an output device operatively coupled to the processor, a map of the tissue surface and a visual representation of the expected ablation zone in the map of the tissue surface.

In some embodiments, a system may include a field generator configured to generate an electric or magnetic field; a signal generator configured to generate a pulse waveform for ablating tissue; an output device; and a processor operatively coupled to the field generator, the signal generator, and the output device, the processor configured to: activate the field generator to generate the electric or magnetic field such that signals are received by a receiver coupled to an ablation device disposed adjacent to a tissue surface; obtain processed data associated with the signals; determine a position and an orientation of the ablation device based on the processed data; determine an expected ablation zone of the ablation device in the tissue surface based on the position and the orientation of the ablation device; cause the output device to display a map of the tissue surface and a visual representation of the expected ablation zone in the map of the tissue surface; and in response to the expected ablation zone corresponding to a desired ablation zone, activate the signal generator to generate the pulse waveform to be delivered to the ablation device such that the ablation device produces an ablated zone corresponding to the expected ablation zone.

DETAILED DESCRIPTION

Figure 1A:
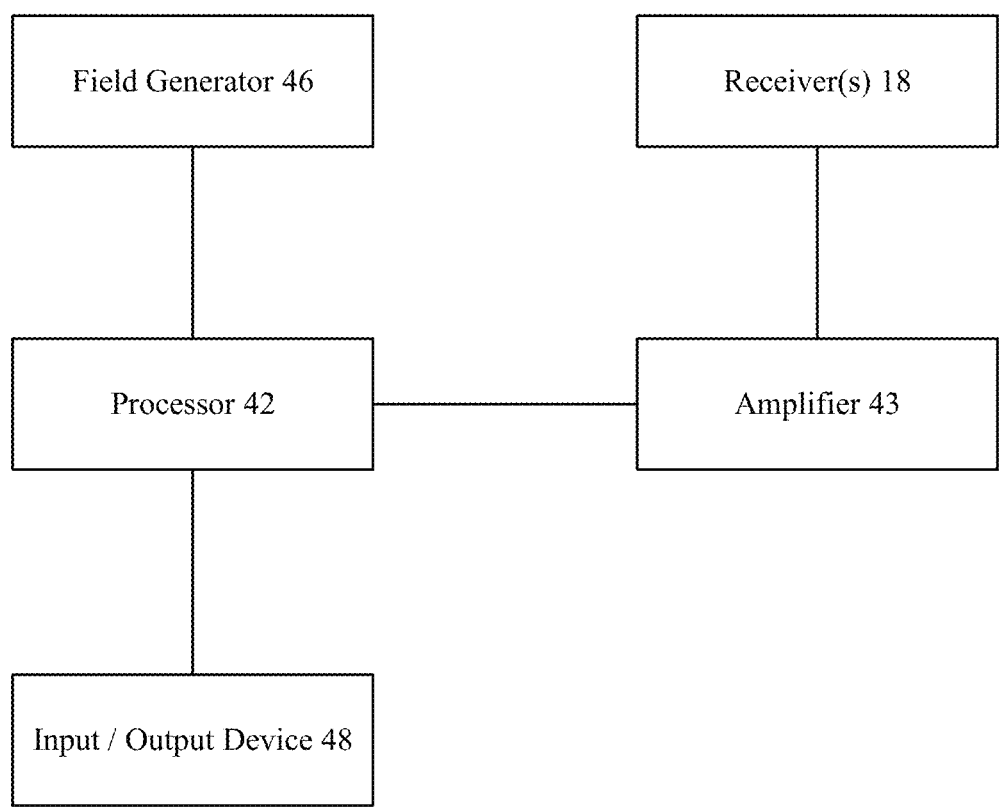
FIG. 1A is a schematic diagram of a mapping/device localization system, according to embodiments.

Described herein are systems, devices, and methods for selective and rapid application of pulsed electric fields to ablate tissue by irreversible electroporation. Generally, the systems, devices, and methods described herein may be used to generate lesion lines with an ablation device (e.g., a focal ablation device).

In some embodiments, the systems, devices, and methods described herein provide spatial tracking of an ablation device (e.g., catheter) in a body cavity to aid tissue ablation, such as the generation of contiguous and transmural lesion lines with a focal ablation catheter. Such spatial tracking can, for example, provide real-time tracking of the spatial location and orientation of the ablation device. Systems, devices, and methods incorporating spatial tracking functionality may enable real-time procedure planning and may be applied to the context of pulsed electric field ablation procedures with delivery of high voltage pulse waveforms to generate lesions using irreversible electroporation.

Pulsed electric field ablation for cardiac tissue ablation has been demonstrated recently to be a suitable modality for the rapid and effective generation of ablation lesions. In the cardiac context, focal ablation, or the creation of discrete local lesions, is a relevant application of pulsed electric field ablation. In a clinical catheter laboratory, electroanatomical mapping systems (e.g., the CARTO® system manufactured by Biosense Webster Inc., or the NavX™ system manufactured by Abbott Laboratories) can be used to provide three-dimensional visualization feedback for a catheter device positioned in the cardiac anatomy or chambers.

An electromagnetic tracking sensor may be integrated into a catheter device using electrodes configured to track the device position (e.g., in real time) within a three-dimensional volume of interest. Suitable electromagnetic tracking or localization systems for some medical applications include, for example, systems and sensors manufactured by Northern Digital Inc. Using a catheter endowed with such a sensor endocardially to navigate to different locations within a cardiac chamber, location data of a catheter electrode, and/or ECG signals recorded from the electrodes may be used to reconstruct the surface anatomy of a cardiac chamber.

Additionally or alternatively, a device location tracking system may determine a location of a device (e.g., a catheter) using an electric field or voltage gradients generated by a set of surface electrode patches on a patient, e.g., with potential differences set up between the surface electrode patches. With at least three such independently paired potential differences not all in the same plane, the three-dimensional location of an electrode may be estimated based on the voltage potentials measured by an electrode or sensor relative to one or more of the surface patches, or equivalently, impedance measurements may be estimated based on measured currents and/or voltages. Suitable techniques and methods of estimating spatial locations using such potential differences or voltage gradients of a set of electrodes, also termed impedance tracking or impedance-based localization systems, are incorporated in electroanatomical mapping systems such as the NavX™ system manufactured by Abbott Laboratories, the Rhythmia™ system manufactured by Boston Scientific Inc., or the CARTO® system manufactured by Biosense Webster Inc. In some embodiments, when a catheter device includes an electromagnetic sensor for electromagnetic tracking and is further used with an impedance tracking system, the locations of electrodes on the catheter may be more accurately estimated than by the use of impedance tracking without electromagnetic tracking.

Given a focal catheter configured to deliver pulsed field ablation lesions (e.g., lesions produced by irreversible electroporation) with a high voltage pulse waveform, the characteristics of a lesion (e.g., spatial extent and geometry) delivered using such a catheter with a given pulsed field ablation waveform and at given voltages may be determined using computational modeling and/or lesion data from studies or past procedures (e.g., preclinical or animal studies and/or procedures). Depending on the electrode geometry of the focal catheter, the lesion geometry generated by such an ablation generally depends at least in part on device orientation with respect to a local tissue surface or wall.

Systems and methods described herein relate to displaying expected lesion geometries or ablation zones on anatomical maps or surface renderings, which can enable a series of lesions (e.g., contiguous and/or transmural) to be efficiently generated in a predetermined anatomical region. In some embodiments, a focal ablation catheter configured to generate pulsed electric field ablation lesions can take a variety of geometric forms. In some embodiments, the methods, systems, and devices disclosed herein may comprise one or more of the methods, systems, and devices described in U.S. application Ser. No. 16/375,561, filed on Apr. 4, 2019, and titled "SYSTEMS, DEVICES, AND METHODS FOR FOCAL ABLATION," the contents of which are hereby incorporated by reference in its entirety.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Systems

Disclosed herein are systems and devices configured for generating focal ablation lesions in tissue. Generally, a system described here for ablating tissue with high voltage pulse waveforms may include a device tracking or localization component, ECG recording or monitoring component, cardiac stimulator, and ablation component. The systems, methods and implementations described in the present disclosure apply to synchronous or asynchronous ablation delivery. Furthermore, as described herein, the systems and devices may be deployed endocardially and/or epicardially to treat cardiac fibrillation.

FIG. 1A is a schematic diagram of a mapping or localization system (10) (e.g., electromagnetic tracking) including a field generator (46) including a set of transmitters configured to generate an electromagnetic field. In embodiments including an impedance-based tracking system, the electric field generator (46) may include a set of electrode patches between subsets of which electric potential differences are maintained over a range of frequencies. In embodiments including an electromagnetic tracking system (10), the electric field generator (46) may include a set of transmitter coils each configured to generate a time-varying magnetic field. The generated electric or magnetic fields (respectively, for an impedance-based tracking system or for an electromagnetic tracking system, or both types of systems) are received generally as signals (voltages, currents or both) by a set of receivers (18) of a medical device (e.g., ablation catheter, focal ablation device (110)) to be spatially tracked. The received signals may be amplified by an amplifier (43) and then digitized and processed by one or more processors (42). The processor(s) (42) may also be configured to control or drive the electric field generator (46). The processor(s) (42) may be configured to estimate and/or determine the position and/or orientation of the medical device based on the received signals. The estimated position and orientation information may be displayed on an input/output device (48) (e.g., graphic display (160)) in the form of a visual rendering of the spatially tracked device. In some embodiments, the input/output device (48) may allow a user to interact with the rendering (e.g., view it from different perspectives) and/or visualize the device together with a constructed or imaged subject anatomy.

Figure 1B:
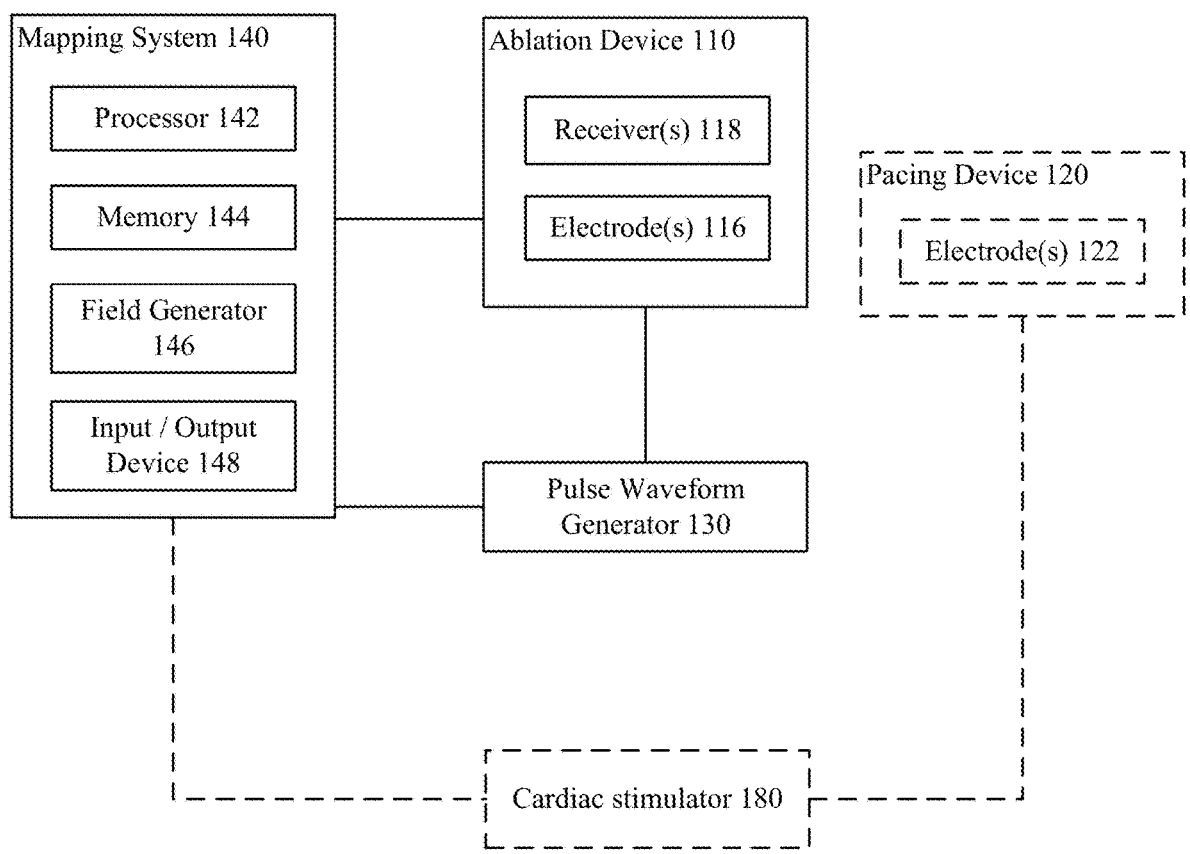
FIG. 1B is a schematic diagram of an electroporation system, according to embodiments.

FIG. 1B is a schematic diagram of an electroporation system (100) including an ablation device (110), a mapping system (140), a pulse waveform generator (130), and optionally a cardiac stimulator (180). The ablation device (110) may include one or more electrodes (116) configured to generate pulsed electric fields for pulsed field ablation, e.g., via irreversible electroporation. The ablation device (110) can include one or more receivers (118) configured to receive signals (voltages, currents or both), e.g., from a field generator (146) of the mapping system (140), as further described below. In some embodiments, the ablation device (110) can be an ablation catheter that can be introduced into cardiac anatomy, e.g., an endocardial space of an atrium. The distal portion of the ablation catheter can include the electrode(s) (116) configured to deliver ablation energy (e.g., pulsed electric field energy) to nearby tissue. One or more electrode(s) (116) can be jointly wired or independently addressable. In operation (e.g., during an ablation procedure), voltages (e.g., ultra-short, high voltage pulses) may be applied to a selected subset of the electrodes of the ablation device. Each electrode (116) may include an insulated electrical lead configured to sustain an electrical potential difference of between about 200 V to about 3,000 V across its thickness without dielectric breakdown. In some embodiments, the electrode(s) (116) may include a plurality of electrodes that can be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like, without limitation. Further details and example embodiments of an ablation device (110) are provided in later figures.

The ablation device (110) can be operatively coupled to a mapping system (140). The mapping system (140) can include components that are functionally and/or structurally similar to the ablation mapping system (10), as described above with respect to FIG. 1A. For example, the mapping system (140) may include a processor (142), memory (144), field generator (146), and an input/output device (148). The processor (142) can be any suitable processing device configured to run and/or execute a set of instructions or code. The processor (142) may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like. The processor (142) can be configured to control field generator (146) to generate one or more electric, magnetic, or electromagnetic fields. In some embodiments, the field generator (146) can include a set of electrode patches externally disposed on a patient that can be used to generate electric fields. In some embodiments, the field generator (146) can include a set of transmitter coils configured to generate a time-varying magnetic field. The fields generated by the field generator (146) can be received by receiver(s) (118). In some embodiments, receiver(s) (118) can be integrated into the ablation device (110). For example, electrodes on the device can sense voltage potentials generated by the field generator(s) (146). Alternatively or additionally, receiver(s) (118) can be disposed nearby, within, or adjacent to the ablation device (110), e.g., on a probe or a sensor disposed within a lumen of the ablation device (110). The processor (142) can be configured to determine a position, orientation, and/or configuration of the ablation device (110) or other tracked device. For example, and as further described in further embodiments below, the processor (142) can process data received by receiver(s) (118) and/or analyze that data to determine the position or orientation of the ablation device (110) relative to a cardiac surface or wall, or a configuration (e.g., shape, state of deployment) of the ablation device (110) as it is deployed within the cardiac space. The processor (142) can be configured to determine an expected ablation zone in target anatomy given information associated with the patient, the ablation device (e.g., position, orientation, and/or configuration), the pulse waveform parameters, etc., as further described in the example embodiments below. During generation of contiguous and transmural lesions, the processor (142) can be configured to determine expected ablation zones and/or ablated zones.

Memory (144) can be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor (142) to execute modules, processes and/or functions, such as field generation and/or location and orientation determination.

Input/output device (148) can be used to present information and/or receive information from a user and/or other compute devices (e.g., remote compute devices that are operatively coupled to the electroporation system (100) via a wired and/or wireless connection. In some embodiments, the processor (142) (or another processor) can be configured to generate information and control the input/output device (148) to present that information, e.g., using a display, audio device, projector, etc. The input/output device (148) can include, for example, a user interface, e.g., a display, an audio device, etc. that enables presentation of outputs to a user and/or receipt of input from the user. In some embodiments, the input/output device (148) can display a visual representation of specific anatomy (e.g., cardiac anatomy) along with a visual representation of a tracked device (e.g., the ablation device (110)) within that anatomy. In operation (e.g., during an ablation procedure), the visual representation can display the position, orientation, and/or configuration of the tracked device as it moves through target anatomy, e.g., in real-time (e.g., within fractions of a second). In some embodiments, the input/output device (148) can be used to receive inputs from a user that specify pulse waveform parameters (e.g., voltages, durations, delays, etc.), properties or characteristics of the ablation device (e.g., type of ablation device, deployment state, etc.) and/or other information that may assist in determining an expected ablation zone. In some embodiments, input/output device (148) can be configured to display expected ablation zones and/or ablated zones, e.g., in real time during an ablation procedure. In some embodiments, input/output device (148) can be configured to display different features or components (e.g., surrounding anatomical structure, ablation device, expected ablation zone, and/or ablated zone) using different markings, patterns, visual renderings, and/or colors to show during components as overlaying other components.

The pulse waveform generator (130) may be configured to generate ablation pulse waveforms for irreversible electroporation of tissue, such as, for example, pulmonary vein ostia. For example, the pulse waveform generator (130) may generate and deliver a pulse waveform to the ablation device (110), which generates a pulsed electric field that can ablate tissue. In some embodiments, the pulse waveform generator (130) is configured to generate the ablation pulse waveform in synchronization with a cardiac cycle of a heart (e.g., within a common refractory window of an atrial pacing signal and a ventricular pacing signal). For example, in some embodiments, the common refractory window may start substantially immediately following a pacing signal (or after a very small delay) and last for a duration of approximately 250 milliseconds (ms) or less thereafter. In some embodiments, an entire pulse waveform may be delivered within this duration, while in other embodiments, portions of the pulse waveform may be delivered within this duration with other portions being delivered during common refractory windows of a subsequent cardiac cycle. In such embodiments, the synchronization with the cardiac cycle can be achieved through the use of pacing or by appropriate gating of ablation delivery to R-wave detection based on an ECG recording.

In some embodiments, a cardiac stimulator (180) can be configured to generate pacing signal(s) and provide these to an optional pacing device (120) disposed near the target anatomy. Pacing device (120) can include a set of electrode(s) 122 that can receive the pacing signals and deliver them the cardiac anatomy, e.g., to pace the heart. One or both of atrial and/or ventricular pacing signals can be generated or delivered to the heart. In some embodiments, pacing device (120) can be configured to sense and/or analyze information (e.g., cardiac signals) regarding the patient, and provide this information to one or more of the mapping system (140) and/or pulse waveform generator (130) to further assist with controlling operation of those devices (e.g., initiating or interrupting pulse waveform delivery, determining expected ablation zones and/or ablated zones, etc.).

In some embodiments, the cardiac stimulator (180) and pulse waveform generator (130) may be in communication with one another (e.g., for coordinating timing of the pulse waveform delivery, pacing signal delivery). In some embodiments, the cardiac stimulator (180) may be integrated with the pulse waveform generator (130) in a single console. In some embodiments, the cardiac stimulator (180) and the pulse waveform generator (130) may be in communication with other devices, e.g., mapping system (140) or remote compute devices, directly or via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution.

In some embodiments, the pulse waveform generator (130) and/or cardiac stimulator (180) can be operatively coupled to the mapping system (140) such that information regarding the pulse waveform, pacing signals, and/or sensed signals (e.g., sensed cardiac signals from the pacing device (120)) can be provided to the mapping system (140), e.g., to assist with device localization and/or expected ablation determination. In some embodiments, the mapping system (140) and/or processor(s) associated with the pulse waveform generator (130) and/or cardiac stimulator (180) can be integrated into one or more controllers that can function to control the component(s) of each of these devices.

While not depicted, the cardiac stimulator (180) and the pulse waveform generator (130) can include one or more processor(s), which can be any suitable processing device configured to run and/or execute a set of instructions or code, similar to processor (142).

While not depicted, the cardiac stimulator (180) and the pulse waveform generator (130) can include one or more memory or storage device(s), similar to memory (144). The memory may store instructions to cause the processor of any one of the cardiac stimulator (180) and the pulse waveform generator (130) to execute modules, processes and/or functions, such as pulse waveform generation and/or cardiac pacing.

Figure 2A:
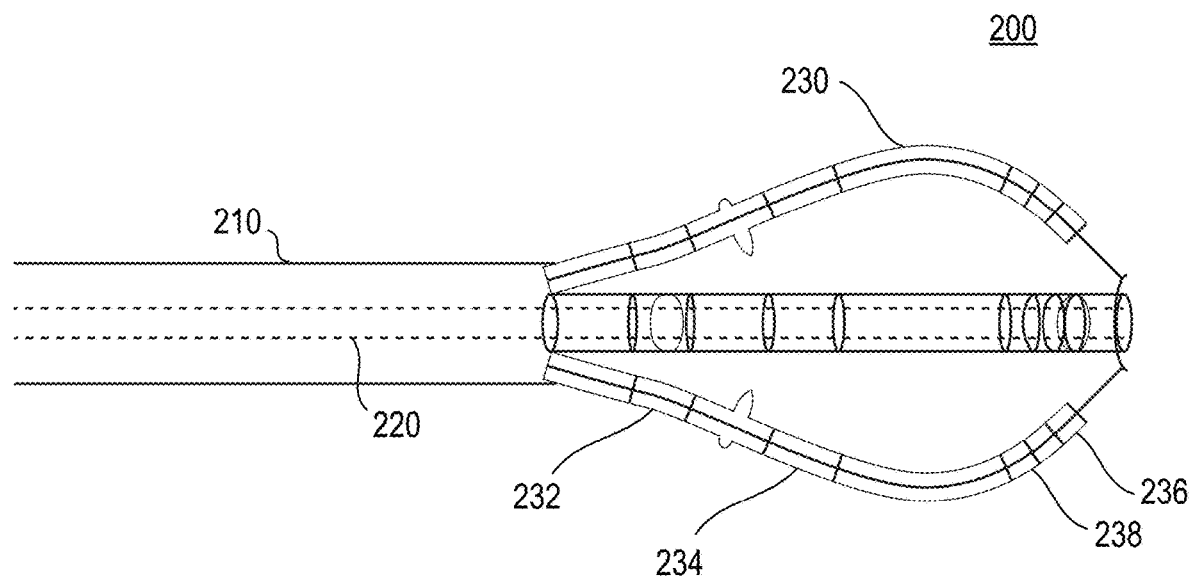
FIG. 2A is a side view of an ablation catheter, according to embodiments.
Figure 2B:
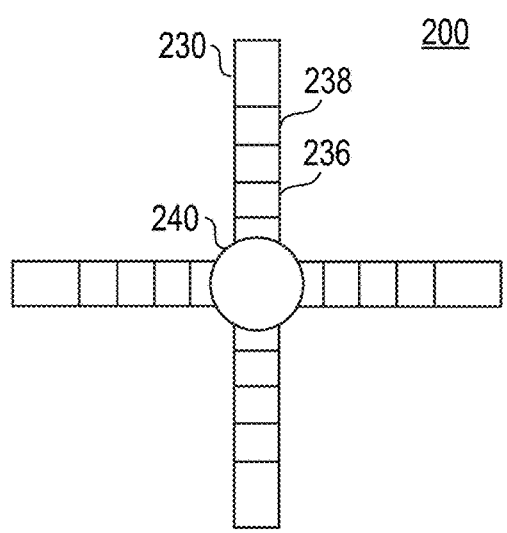
FIG. 2B is a front view of the ablation catheter depicted in FIG. 2A.

FIGS. 2A and 2B are schematic illustrations of an embodiment of an ablation device (e.g., focal ablation device). FIG. 2A illustrates a catheter device (200) configured to receive a pulse waveform and generate an electric field for ablating cardiac tissue. The ablation device (200) may include an outer catheter shaft (210), an inner catheter shaft (220), a set of splines (230), and electrodes (232, 234, 236, 238). The outer catheter shaft (210) may include a distal end where proximal ends of the set of splines (230) (four splines in FIGS. 2A and 2B) are coupled symmetrically to inner catheter shaft (220) within a lumen of the outer catheter shaft (210). In some embodiments, the inner catheter shaft (220) may be configured to extend beyond the outer catheter shaft (210). The distal end of the set of splines (230) may be coupled to a distal end of the inner catheter shaft (220) via a distal cap (240) as shown in FIG. 2B. In some embodiments, the inner catheter shaft (220) may be configured to actuate (e.g., deploy, retract) using a control mechanism (e.g., an actuator) such as, for example, a knob or rocker switch in a catheter handle (not shown), which may transition the set of splines (230) (e.g., basket of splines) to bend or change configuration, e.g., from a substantially linear shape to a bulb-like shape, as shown in FIG. 2A. The set of splines (230) may be configured to have a plurality of configurations of different shapes and diameters, from undeployed (e.g., compressed within an outer catheter lumen or in a resting or unconstrained configuration) to partial deployment to full deployment. Stated differently, the set of splines (230) can be deployed over a range of successively larger deployments that expands a largest diameter of a deployed shape of the splines (230) over a range of deployment forms or configurations. For example, the set of splines (220) may transition to a semi-deployed configuration having a diameter between that of an undeployed configuration and the fully deployed configuration.

In some embodiments, one or more of the splines (230) may include one or more of a set of proximal electrodes (232, 234) and distal electrodes (236, 238). In some embodiments, a spline of the set of splines (230) may include between about 1 and about 8, inclusive, proximal electrodes (232, 234) and between about 1 and about 8, inclusive, distal electrodes (236, 238). In some embodiments, the device (200) may include between about 2 and about 12 splines, including all ranges and sub-values in-between.

In some embodiments, an ablation device (e.g., ablation device (110, 200)) may incorporate a receiver (e.g., receiver (118)) implemented as an electromagnetic tracking sensor for tracking a position or orientation of the ablation device. Along with the device configuration calculations as described herein, the electromagnetic localization data may provide refined (e.g., improved) spatial locations of all the device electrodes. In such embodiments, the ablation device can be used to endocardially navigate to different locations within a cardiac camber while collecting location data and/or cardiac data (e.g., recorded using one or more electrodes of the ablation device), which in turn can be used to construct a virtual representation of a surface anatomy of the cardiac camber.

Additionally or alternatively, in some embodiments, an ablation catheter (e.g., ablation device (110)) can include a receiver implemented as an electrode that is configured to measure voltage and/or current induced by electric fields generated by a set of surface patches. In such embodiments, the set of surface patches can be configured to generate electric fields in multiple planes, with voltage and/or current signals being measured by the electrode of the ablation catheter (or impedance estimated using such measurements).

While an ablation device (110) having a basket shape is depicted in FIGS. 2A and 2B, it can be appreciated that ablation device(s) suitable for applications described herein can have a geometry different from that shown in FIGS. 2A and 2B. For example, other example ablation devices can include a linear focal ablation catheter with a set of electrodes disposed along a distal portion of a catheter shaft. Suitable examples of a linear ablation catheter are described in U.S. Provisional Patent Application No. 62/863,588, filed Jun. 19, 2019, titled "Systems, Devices, and Methods for Focal Ablation," the disclosure of which is incorporated herein by reference. The set of electrodes may include a set of distal electrodes and a set of proximal electrodes arranged on a single linear shaft. In some embodiments, the set of distal electrodes may include a distal cap electrode. The distal device geometry may be generally characterized by a set of parameters including, for example, the lengths and diameters of the electrodes, as well as the set of separation distances between adjacent electrodes. Similar to the above described with respect to the ablation catheter shown in FIGS. 2A and 2B, for a given geometric arrangement of electrodes on the focal ablation catheter device, a distal device geometry, or generally the electrode geometry, may be characterized by a set of geometric parameters.

Methods

Also described here are methods for determining an expected ablation zone during a tissue ablation process performed in or near one or more heart chamber(s) using the systems and devices described herein. In an embodiment, the heart chamber(s) may be the left atrial chamber and include its associated pulmonary veins, while the devices and methods described herein can also be used in other cardiac chambers. Generally, one or more catheters may be advanced in a minimally invasive fashion through vasculature to a target location. For example, an ablation device may be advanced through vasculature over a guidewire and through a deflectable sheath. The sheath may be configured for deflection and aid in guiding a focal ablation catheter through vasculature and one or more predetermined targets (e.g., pulmonary vein ostia). A dilator may be advanced over a guidewire and configured for creating and dilating a transseptal opening during and/or prior to use. The methods described here include introducing and disposing an ablation device (e.g., ablation device (110, 200)) in contact with one or more pulmonary vein ostial or antral regions. A pacing signal may be delivered to the heart using a cardiac stimulator (e.g., cardiac stimulator (180)) and/or measure cardiac activity. Spatial characteristics (e.g., position, orientation, configuration) of the ablation device and tissue may be determined and used to generate an expected ablation zone and/or tissue map for display. A pulse waveform may be delivered by one or more electrodes of the ablation device to ablate tissue. In some embodiments, ablation energy may be delivered in synchrony with cardiac pacing. In some embodiments, the voltage pulse waveforms described herein may be applied during a refractory period of the cardiac cycle so as to avoid disruption of the sinus rhythm of the heart. The tissue map including ablated tissue and the expected ablation zone may be updated in real-time on the display as the device is navigated through tissue and additional pulse waveforms are delivered to the tissue.

A pulse waveform may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode subsets. Additionally or alternatively, the pulse waveforms may include a plurality of levels of a hierarchy to reduce total energy delivery, e.g., as described in International Application Serial No. PCT/US2019/031135, filed on May 7, 2019, and titled "SYSTEMS, APPARATUSES AND METHODS FOR DELIVERY OF ABLATIVE ENERGY TO TISSUE," the disclosure of which is incorporated herein by reference. In some embodiments, the ablation devices (e.g., ablation device (110, 200)) described herein may be used for epicardial and/or endocardial ablation. Examples of suitable ablation catheters are described in International Application Serial No. PCT/US2019/014226, incorporated by reference above.

Figure 9A:
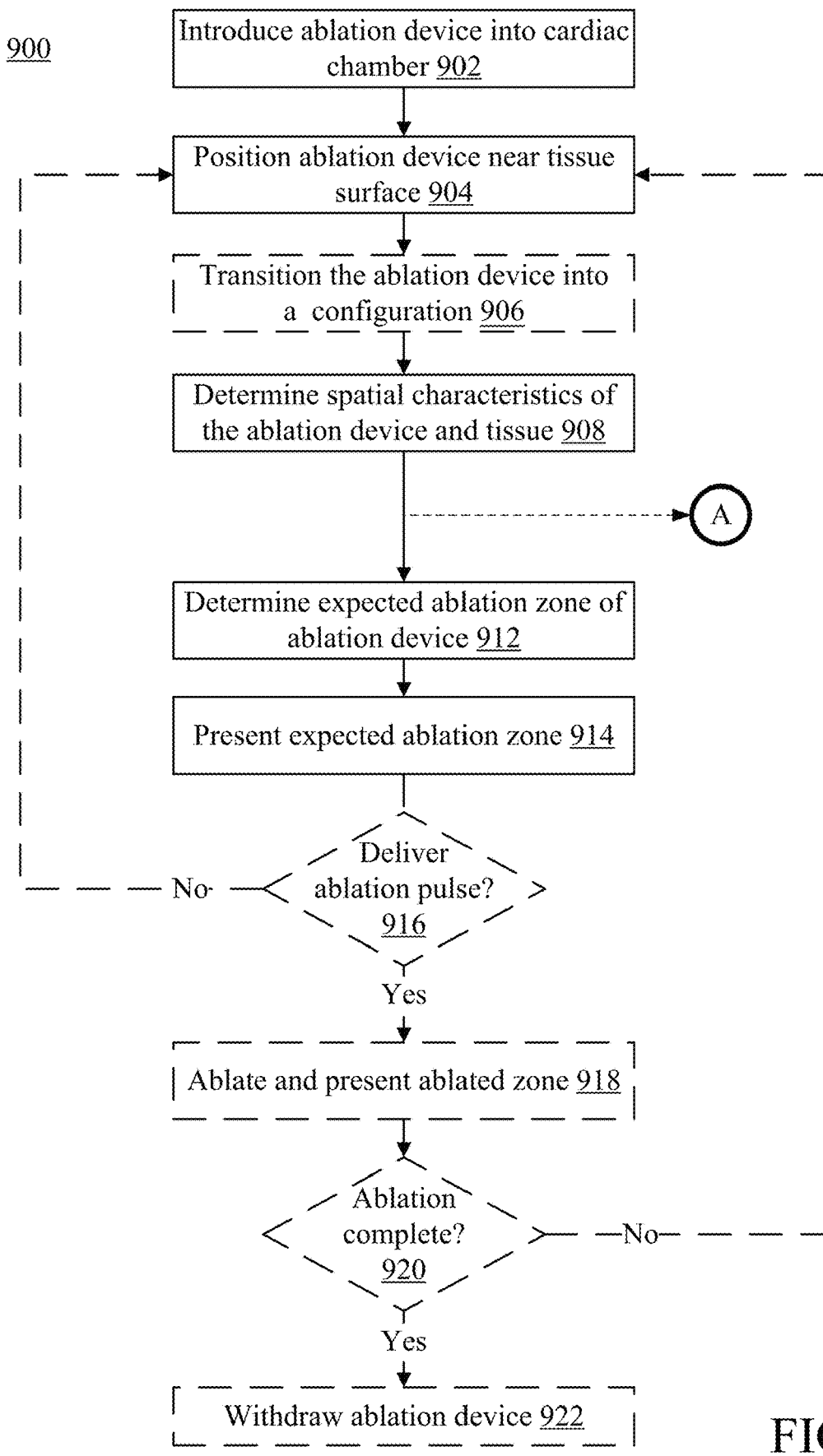
FIGS. 9A and 9B are flowcharts of a tissue mapping and ablation procedure, according to embodiments.

FIG. 9A is an example method (900) of tissue mapping and ablation, according to embodiments described herein. Method (900) can be performed by any of the mapping and/or ablation systems described herein, including, for example, systems (10, 100). In particular, method (900) can be performed by a processor or controller associated with a mapping system or system (e.g., processors (42, 142). The method (900) includes introduction of an ablation device (e.g., ablation device (110, 200)) into a cardiac chamber (e.g., endocardial space) to be disposed in contact with or near the cardiac tissue, at (902). The ablation device may be navigated to a predetermined location, e.g., near a tissue surface, at (904). For example, the ablation device may be positioned near or in contact with an inner radial surface of a lumen (e.g., one or more pulmonary vein ostia) for mapping and/or tissue ablation. Optionally, the ablation device may be transitioned into one of a plurality of configurations (e.g., deployment states), at (906). For example, the ablation device may be transitioned from a fully undeployed configuration to a fully deployed configuration or any configuration in-between (e.g., partially deployed configuration(s)). In some embodiments, the ablation device may include a set of splines, where each spline from the set of splines includes a set or proximal electrodes and a set of distal electrodes such that the set of splines collectively includes a plurality of proximal electrodes and a plurality of distal electrodes. In some embodiments, a user may control an actuator (e.g., handle) to transition a set of splines between different deployment configurations.

In some embodiments, spatial information associated with the ablation device and tissue may be determined, at (908). For example, signals may be received at a receiver (e.g., sensor, electrode, etc.) coupled to or integrated into the ablation device in response to electric and/or magnetic fields generated by a field generator. Data representative of signals received by the receiver may be received at a processor (e.g., processor (42, 142)), which can further process and/or analyze such information. Based on such analysis, spatial information (e.g., position, orientation, configuration) of the ablation device may be determined at the processor.

Figure 3:
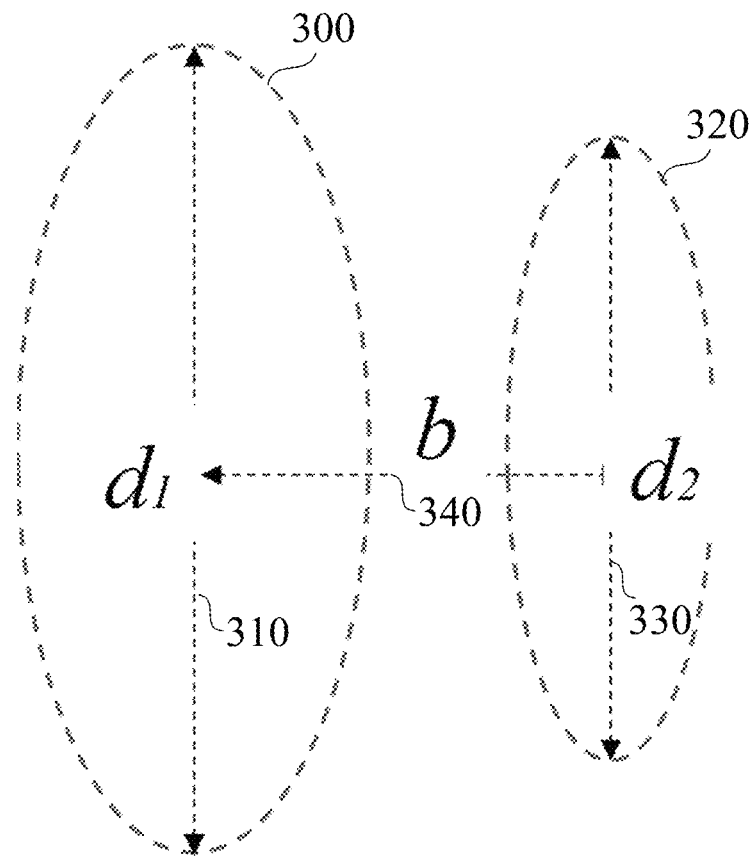
FIG. 3 is a schematic diagram of a cross-section of a set of electrodes of an ablation catheter, according to embodiments.

For example, such analysis can involve determining one or more geometric parameters that characterize the distal end of the ablation device. In some embodiments, with a known distal geometry of a distal portion of an ablation device (e.g., focal ablation catheter), for a given configuration of the splines, the shape of the ablation device may be characterized by a set of geometric parameters. For example, as shown in FIG. 3, the centroids of the proximal electrodes (not shown for the sake of clarity) on each spline lie on a proximal circle (300) and the centroids of the distal electrodes (not shown for the sake of clarity) on each spline lie on a distal circle (320). The proximal and distal circles (300, 320) lie in parallel planes and are separated by a distance b (340). The proximal circle (300) has a diameter $d_1$ (310) and the distal circle (320) has a diameter $d_2$ (330). A geometry of a distal portion of the ablation device may be characterized by these parameters.

In some embodiments, an impedance-based localization system may be configured to generate spatial coordinates of proximal and distal electrodes of an ablation device. Conventional impedance-based localization systems can be prone to error due to tissue inhomogeneities. The localization systems as described herein may generate improved (or refined) spatial coordinate estimates of a distal portion of a focal ablation device. Given the coordinates of the proximal electrodes of an ablation device obtained from an impedance-based localization system, a centroid of the proximal electrodes on each spline may be determined. From this set of centroids on each spline, the centroid $x_1$ of these centroids of the proximal electrodes can be determined. The centroid $x_1$ may be used to calculate a center for a best-fit circle $C_1$ (corresponding to the proximal electrodes) having a diameter $d_1$ that may be calculated using, for example, a least-squares fit. Likewise, the centroids of the distal electrodes of the set of splines can be determined, and a centroid $x_2$ of the centroids of the distal electrodes can be determined. The centroid $x_2$ can be used to calculate a center for a best-fit circle $C_2$ (corresponding to the distal electrodes) having a diameter $d_2$. A diameter $d_1$ of the centroid $x_1$ and a diameter $d_2$ of the centroid $x_2$ may be determined. A distance b between the centroids $x_1$ and $x_2$ may be calculated.

A configuration of the ablation device may be determined based on the diameter $d_1$, the diameter $d_2$, and the distance b, and the orientation of the ablation device may be defined using the centroids $x_1$ and $x_1$. In particular, given a set of known deployment configurations $\{F_i\}$ of the ablation device (with index i labeling the configurations), each with corresponding parameters $\{d_{1,i}, d_{2,i}, b_i\}$, the closest configuration $\{F^*_i\}$ may be calculated, for example, by finding the configuration with minimal error or cost $S_i$ using:

$$S_i = (d_{1,i} - d_1)^2 + (d_{2,i} - d_2)^2 + (b_i - b)^2$$

In embodiments where a focal ablation catheter device does not incorporate an electromagnetic sensor, the device orientation may be defined in part by the unit vector v as follows:

$$v = \frac{(x_1 - x_2)}{|x_1 - x_2|}$$

Furthermore, the unit vector $w = (p_1 - x_1)/|p_1 - x_1|$ from the centroid $x_1$ to the centroid $p_1$ of proximal electrodes on a fiducial spline (for example, a first spline) together with v may fully define the device orientation. The device configuration, as obtained above, and the device orientation may provide improved spatial locations of each of the device electrodes.

Figure 9B:
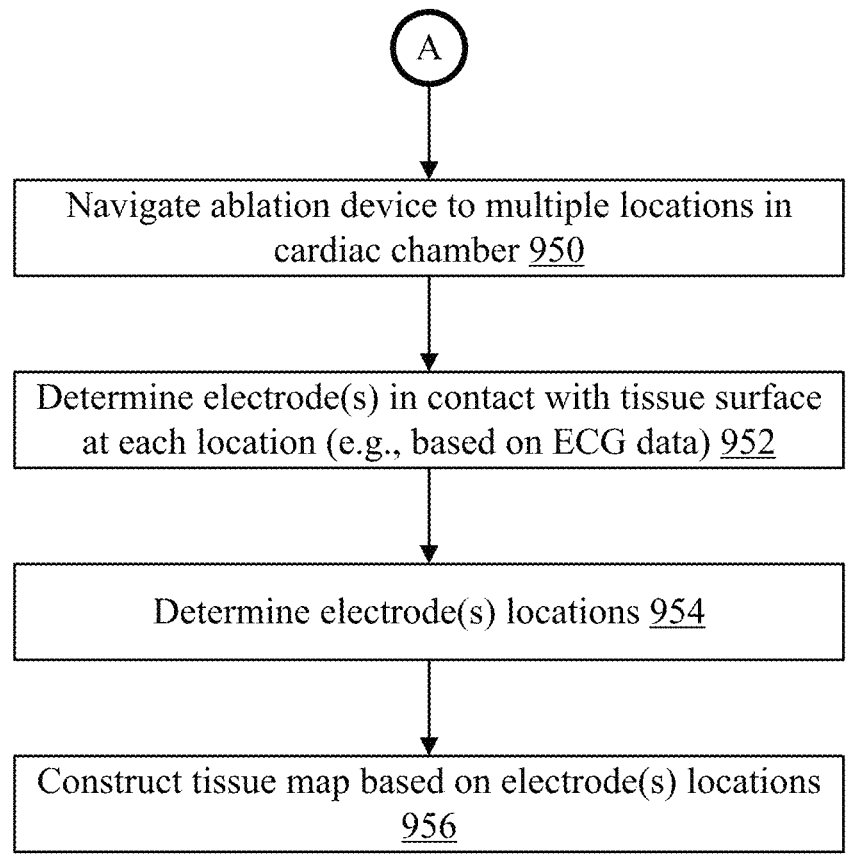

Optionally, a surface anatomy of a cardiac chamber may be constructed (e.g., simulated) using the device location and/or tracking systems described herein. For example, as depicted in FIG. 9B, the focal catheter device may be navigated to different locations in a cardiac chamber, at (950), and based on intracardiac ECG recordings from the catheter electrodes, the electrode(s) in contact with a tissue surface may be determined at any time (for example, based on ECG amplitude, timing or other criteria), at (952). After determining those electrode(s) in contact with the tissue surface, at (954), the discrete electrode locations of those electrode(s) can be determined based on the device geometry and sensed location, as described above with reference to FIGS. 3 and 9A. The electrode locations may be acquired as a point for an anatomical map or surface reconstruction. As the device is navigated to various locations at the endocardial chamber surface, a multiplicity of such points (e.g., locations of electrodes in contact with the tissue surface), or a point cloud, may be acquired to form the basis for a tissue map. In some embodiments, a tissue map may be generated, at (956). For example, a point cloud including a plurality of points may be generated, at (954), where each point from the plurality of points corresponds to a location of the electrode identified at a different location from the plurality of locations. The map of the tissue surface may be constructed using the point cloud, at (956).

Figure 10:
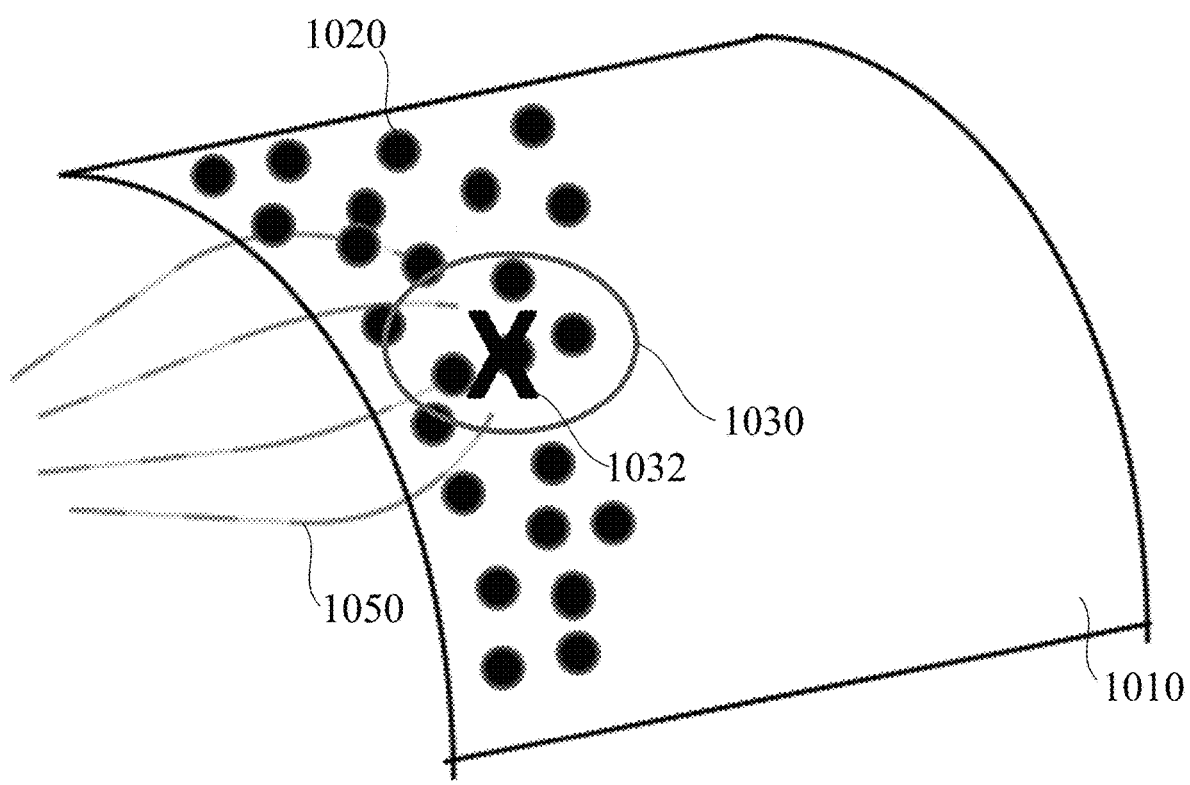
FIG. 10 is a perspective view of an anatomical surface map, according to embodiments.

A portion of such a representation (e.g., tissue map) is illustrated in FIG. 10, where an endocardial anatomical surface reconstruction (1000) is constructed using a point cloud including points (1020) indicative of the locations of electrode(s) that were in contact with the tissue surface at the multiple locations to which the ablation device was navigated. Based on these points, a surface triangulation or mesh may be used to generate surface renderings, including light and shadow effects, perspective, etc.

In some embodiments, an anatomical map of the cardiac chamber can be acquired using other devices (e.g., imaging devices, etc.), and the anatomical map can be provided to the mapping and ablation systems described herein. In such embodiments, the ablation device can optionally be used to confirm the accuracy of the anatomical map, e.g., using the method depicted in FIG. 9B. Alternatively, 950-956 can be omitted, and systems described herein can rely on an anatomical map that is provided by an external source.

Figure 11:
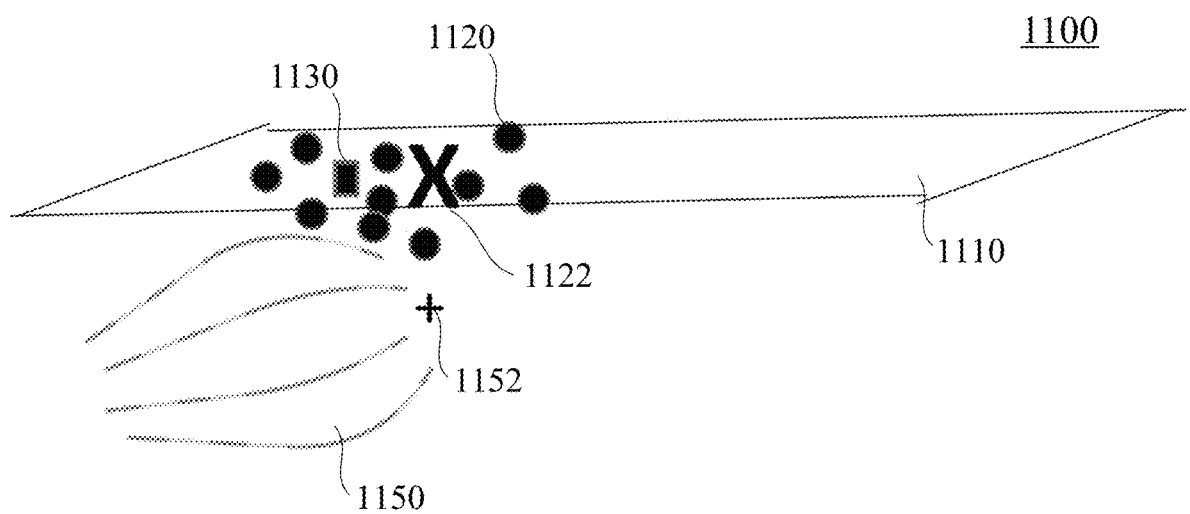
FIG. 11 is a perspective view of an anatomical surface map according to embodiments.
Figure 12:
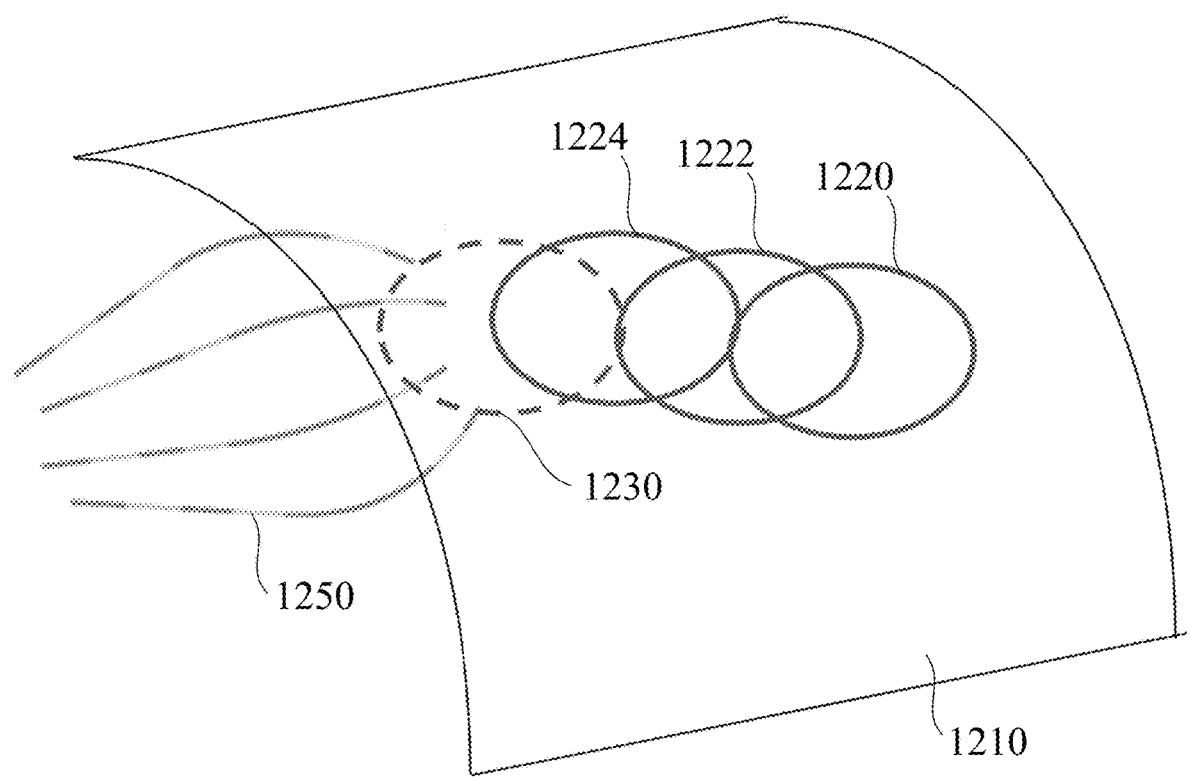
FIG. 12 is a perspective view of an anatomical surface map, according to embodiments.

Referring back to FIG. 9A, the method (900) further includes determining an expected ablation zone of the ablation device, at (912), and presenting the expected ablation zone (e.g., visually on a display), at (914). Optionally, a portion of the ablation device can also be presented along with the expected ablation zone. For example, the output device may display a visual representation of the ablation device relative to the map of the tissue surface based on the position and the orientation of the ablation device. FIG. 10 illustrates a distal portion (1050) of a focal ablation catheter device including a basket of splines near or at the endocardial surface (1010). FIG. 10 further depicts an expected ablation zone (1030) displayed on the surface reconstruction (1000) corresponding to the location of the focal ablation device at the endocardial surface. The ablation zone (1030) has a center (1032) that may be located as described herein. FIGS. 11 and 12 depict respective ablation devices (1150, 1250) having the determined position and orientation relative to the tissue surface map (1110, 1210).

In some embodiments, the expected ablation zone can be determined at a processor (e.g., processor (42, 142)) based on the position and the orientation of the ablation device, as further described below. For example, the expected ablation zone can be determined by determining a nearest distance from the ablation device to the tissue surface, identifying a set of points from the plurality of points within a predefined distance from a distal end of the ablation device when the nearest distance is less than a predefined value, determining a centroid of the set of points, determining a local tangent plane to a surface extending through the centroid, and determining a center of the expected ablation zone based on the position and the orientation of the ablation device relative to the local tangent plane, the center representing a location of the tissue surface having a maximum depth of ablation. Furthermore, an expected ablation zone can be based on one or more pulse waveform parameters (e.g., voltage, duration, delays, number of pulses, number of pulse groups, etc.) that may modify, for example, a size and depth of an expected ablation zone.

To illustrate an example of determining the expected ablation zone, FIG. 11 depicts an ablation device (1150) (e.g., a focal ablation catheter) at an endocardial surface represented by a point cloud comprising a multiplicity of points, including points (1120). As depicted, the ablation device can be in an oblique orientation and be partially deployed (e.g., similar to FIG. 5 and other figures described further below). The distal tip (1152) of the device is also shown in FIG. 11. Based on the current location of the distal tip (1152), and if the nearest distance from the device to the endocardial surface is less than a pre-defined separation, a local set of points in the point cloud within a pre-defined distance D from the device tip may be identified by points (1120). For example, the pre-defined separation may be smaller than about 4 mm and the pre-defined distance can be smaller than about 3 cm. While other points in the point cloud are not depicted, it can be understood that the point cloud can include additional points (not depicted) that are not within the local set of points.

A centroid (1122) of this local set of points may be calculated. A local tangent plane (1110) to the surface passing through the local centroid (1122) is determined. For example, such a plane may be determined by solving an optimization problem. If the local set of points (1120) is the centroid (1122) is $x_c$, and the unit normal to the local tangent plane (1110) is n, then the distance of each local point to the tangent plane (1110) is given by:

$$q_i = (y_i - x_c) \cdot n$$

A cost function can be defined as the sum of such squared distances:

$$C = \sum_i q_i^2 = n^T A n$$

where the matrix A is defined as the sum (over the local set of points) of outer products $$A = \sum_i (y_i - x_c)(y_i - x_c)^T$$

In some embodiments, it is desired to find the normal n to the local tangent plane that minimizes the cost C. Furthermore, since n is a unit normal, it satisfies the constraint $n^T n = 1$. Introducing an appropriate Lagrange multiplier $\lambda$, this leads to the constrained cost function:

$$C' = n^T A n - \lambda(n^T n - 1)$$

In some embodiments, C' may be minimized with respect to n and $\lambda$. For example, performing the minimization leads to the eigenvalue equation:

$$An = \lambda n$$

The unit eigenvector n* corresponding to the smallest eigenvalue of the matrix A is the desired solution for the normal to the local tangent plane (1110). Thus, the local tangent plane (1110) is determined.

Once the local tangent plane is known, based on known properties of the ablation zone (and its center) depending on the orientation of the distal device geometry with respect to the local tangent plane and/or deployment configuration, the ablation zone center (1130) may be determined. Thereafter, for a given device positioning or placement at the endocardial surface, the expected ablation zone can be rendered in the local tangent plane. In some embodiments, the expected ablation zone can be projected onto the surface rendering itself and be depicted as one or more of a contour on the surface, colored patch, or other graphical indicator (e.g., be projected or rendered in a map of the tissue, at (914)).

The expected ablation zone can be presented, at (914), according to various methods. For example, a map of the tissue surface and a visual representation of the expected ablation zone in the map of the tissue surface may be displayed via an output device (e.g., input/output device (48, 148) or an output device coupled to an external compute device) operatively coupled to the processor.

Figure 4:
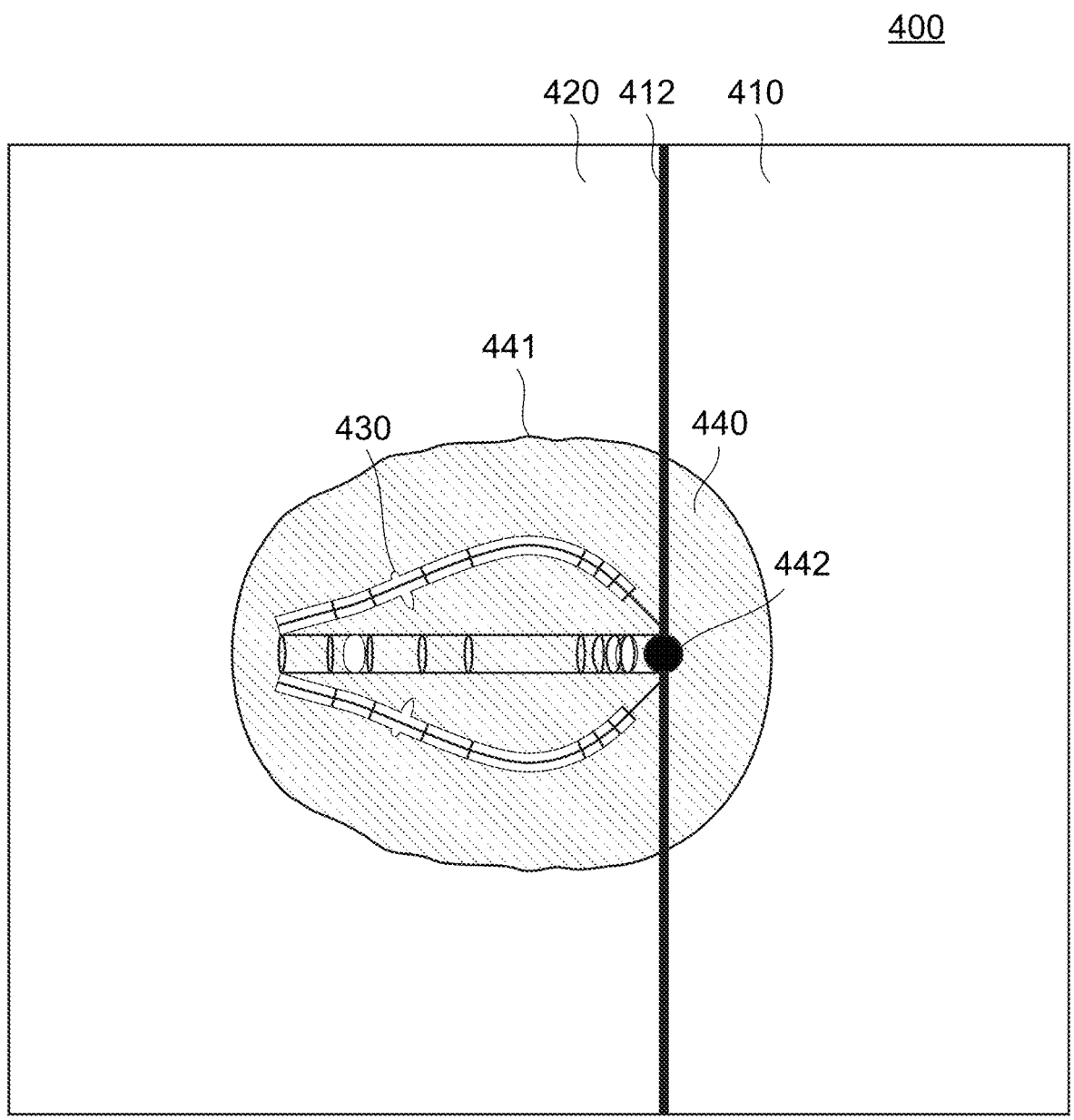
FIG. 4 is a simulated illustration of an ablation device in patient anatomy, according to embodiments.

In some embodiments, the expected ablation zone can be determined (e.g., at a processor including, for example, processor (42, 142)) by identifying an electrode from the plurality of electrodes that is in contact with the tissue surface (e.g., using ECG data, as described above), identifying an expected ablation zone shape from a plurality of expected ablation zone shapes based on the position and the orientation of the ablation device, and generating the expected ablation zone having a center at a location corresponding to a location of the electrode and based on the expected ablation zone shape, the center representing a location of the tissue surface having a maximum depth of ablation. For example, FIG. 4 provides an illustration of an ablation device (430) (e.g., focal ablation catheter) in contact with a tissue region (410) and a simulated or an expected ablation zone (440) to be generated by pulsed electric field ablation. The tissue region (410) interfaces a blood pool (420) at a tissue wall surface or blood-tissue interface (412) where a catheter device (430) in the form of a partially deployed focal ablation catheter is disposed. In FIG. 4, the distal portion of the device has the form of a basket of splines similar to FIGS. 2A-2B and the device (430) engages the tissue interface (412) in a perpendicular or normal orientation with respect to the blood-tissue interface (412). The device (430) can be configured to generate a pulsed electric field (indicated by field contour (441)) that can produce an expected ablation zone (440) via irreversible electroporation. The expected ablation zone (440) is centered (or has maximal depth) at a tissue surface or interface location (442) that, in this case, corresponds to the location of the distal tip of the catheter device (430).

The shape, size, and/or orientation of the expected ablation zone (440) can be based on the spatial characteristics or geometry of the ablation device. For example, a linear focal device can have an ablation zone whose shape and size can be generally different from that of a focal ablation device. In some embodiments, ablated zones generated by the ablation device (430) can be recorded for the ablation device (430) when the device is in a plurality of positions, orientations, and/or configurations relative to a tissue surface, and the resulting shapes of the generated ablated zones can be recorded and stored for future reference in generating expected ablation zones. In some embodiments, such ablated zones can be generated in experimental environments, e.g., using test subjects/preclinical animal models.

Figure 5:
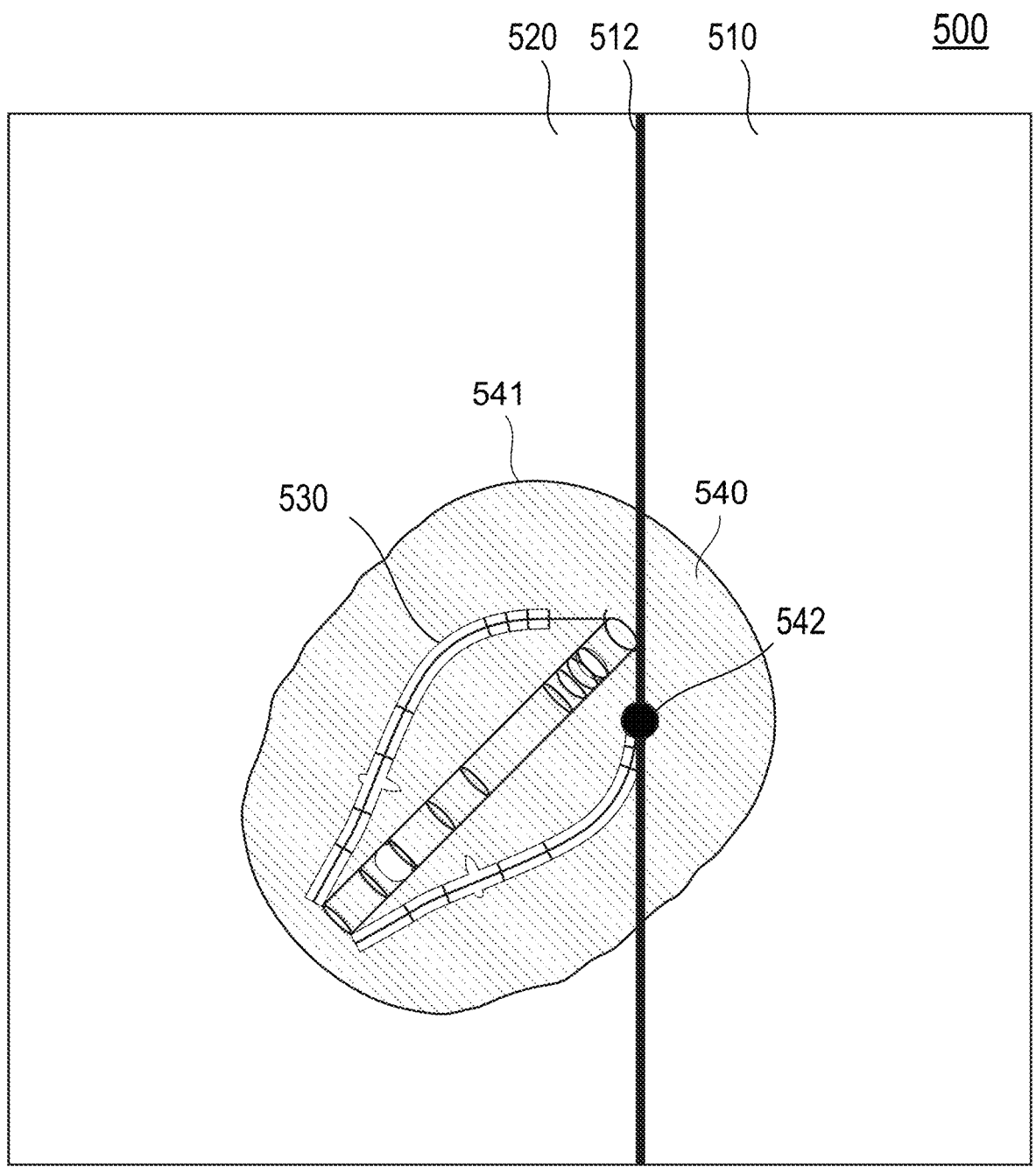
FIG. 5 is a simulated illustration of an ablation device in patient anatomy, according to embodiments.

Further examples of expected ablation zones are depicted in and described with reference to FIGS. 5-8 to illustrate changes to the expected ablation zone depending on ablation device spatial characteristics. FIG. 5 provides an illustration of an ablation device (530) in contact with a tissue region (510) and a simulated or an expected ablation zone (540) to be generated by pulsed electric field ablation. The tissue region (510) interfaces a blood pool (520) at a tissue wall surface or blood-tissue interface (512) where a catheter device (530) in the form of a partially deployed focal ablation catheter is disposed. In FIG. 5, the distal portion of the device has the form of a basket of splines as was already depicted in FIGS. 2A-2B and the device engages the tissue interface in an oblique orientation with respect to the blood-tissue interface (512). The device (530) can be configured to generate a pulsed electric field (indicated by field contour (541)) that can produce an expected ablation zone (540) via irreversible electroporation. The expected ablation zone (540) is centered (or has maximal depth) at a tissue surface or interface location (542) that, in this case, corresponds to the location of the distal-most electrode of the catheter device (530) that is closest to the tissue wall interface (512).

Figure 6:
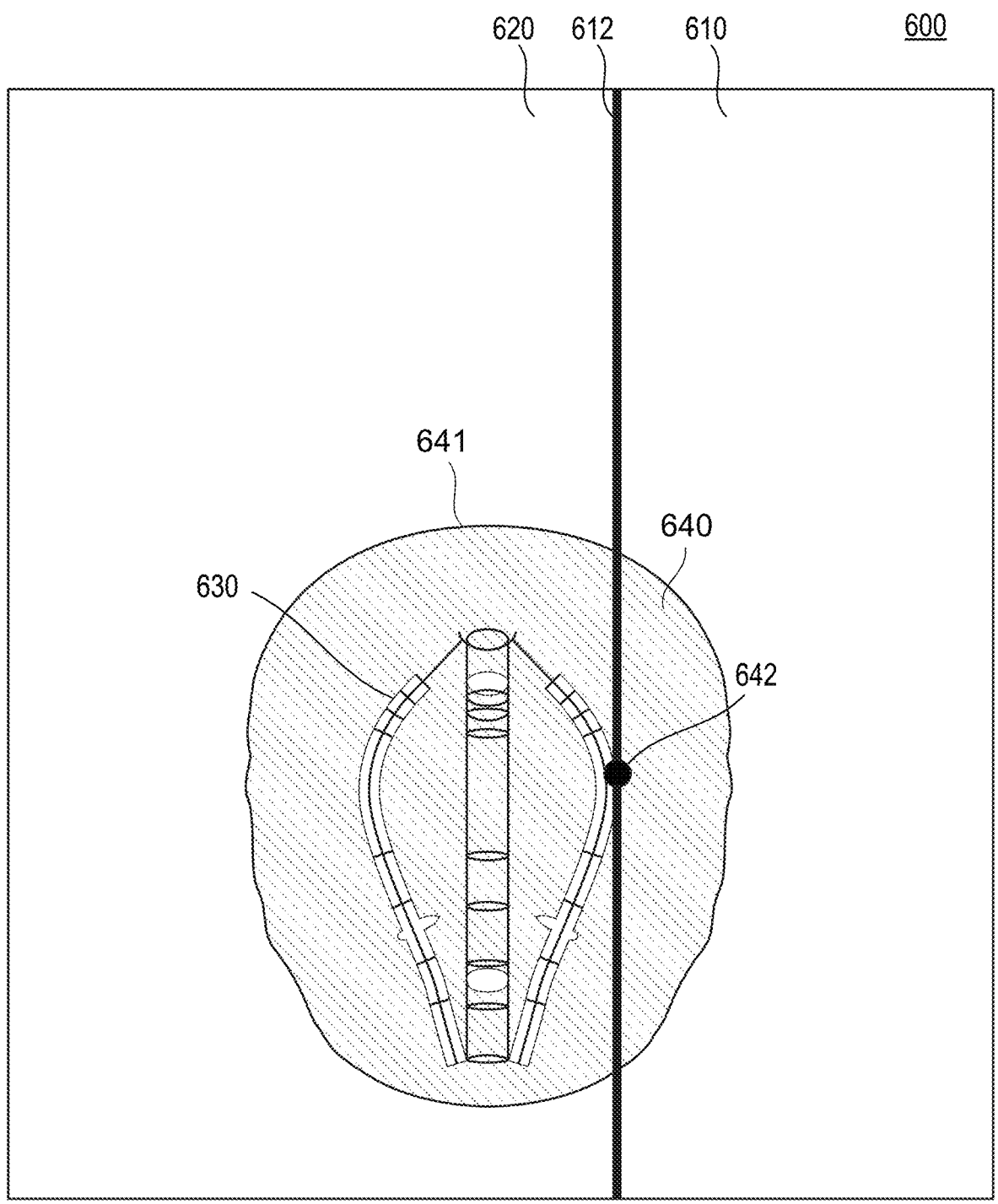
FIG. 6 is a simulated illustration of an ablation device in patient anatomy, according to embodiments.

FIG. 6 provides an illustration of an ablation device (630) in contact with a tissue region (610) and a simulated or an expected ablation zone (640) to be generated by pulsed electric field ablation. The tissue region (610) interfaces a blood pool (620) at a tissue wall surface or blood-tissue interface (612) where a catheter device (630) in the form of a partially deployed focal ablation catheter is disposed. In FIG. 6, the distal portion of the device has the form of a basket of splines similar to FIGS. 2A-2B and the device (630) engages the tissue interface (612) in a parallel orientation with respect to the blood-tissue interface (612). The device (630) can be configured to generate a pulsed electric field (indicated by field contour (641)) that can produce an expected ablation zone (640) via irreversible electroporation. The ablation zone (640) is centered (or has maximal depth) at a tissue surface or interface location (612) that, in this case, corresponds to a location just proximal to the proximal-most edge of the distal electrodes of the catheter device (630) that is closest to the tissue wall interface (612) as illustrated in FIG. 6.

Figure 7:
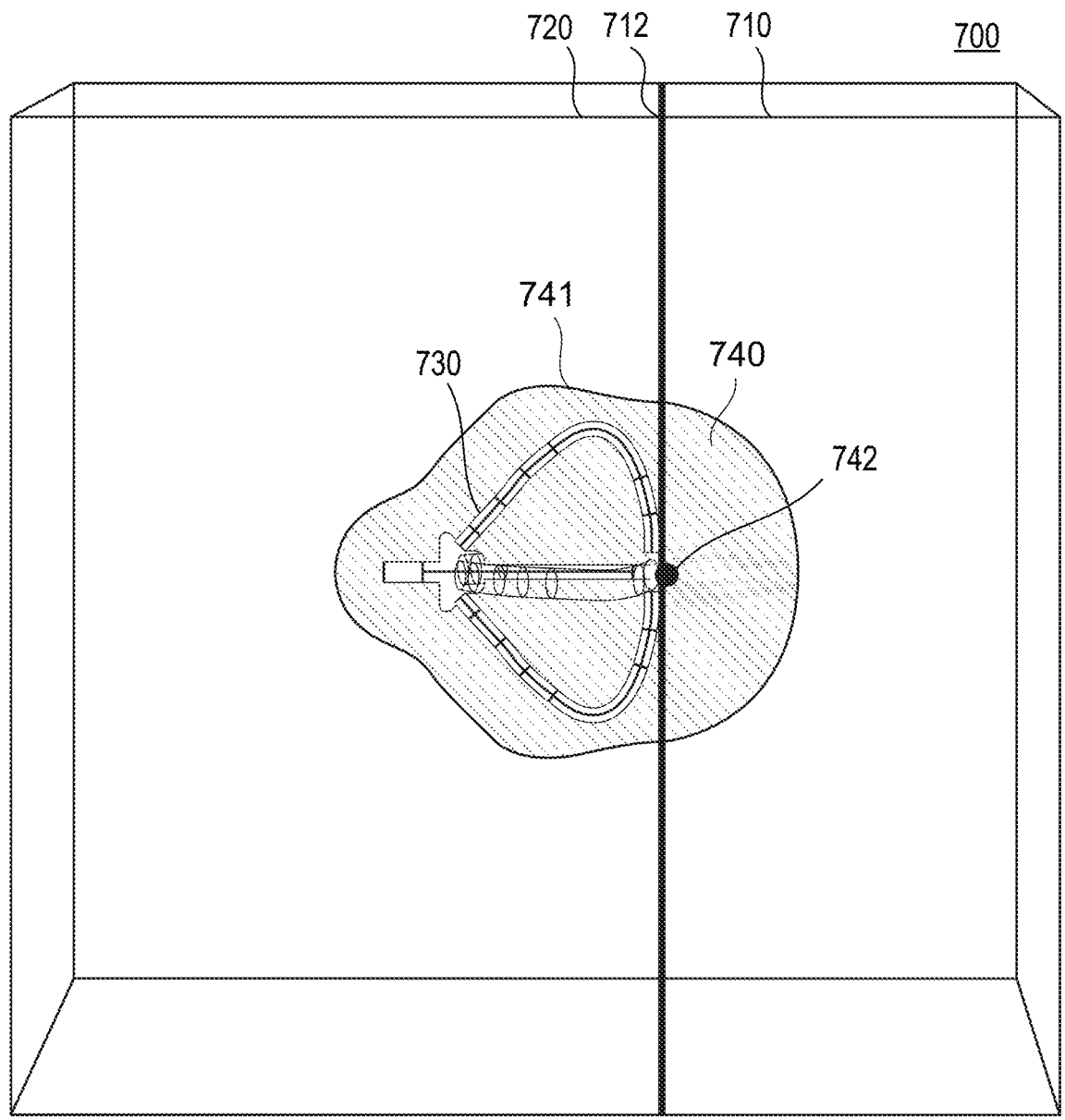
FIG. 7 is a simulated illustration of an ablation device in patient anatomy, according to embodiments.

FIG. 7 provides an illustration of an ablation device (730) in contact with a tissue region (710) and a simulated or an expected ablation zone (740) to be generated by pulsed electric field ablation. The tissue region (710) interfaces a blood pool (720) at a tissue wall surface or blood-tissue interface (712) where a catheter device (730) in the form of a partially deployed focal ablation catheter is disposed. In FIG. 7, the distal portion of the fully deployed device (730) has the form of a basket of splines and the device engages the tissue interface (712) in a perpendicular or normal orientation with respect to the blood-tissue interface (712). The device (730) can be configured to generate a pulsed electric field (indicated by field contour (741)) that can produce an expected ablation zone (740) via irreversible electroporation. The ablation zone (740) is centered (or has maximal depth) at a tissue surface or interface location (712) that, in this case, corresponds to the location of the distal tip of the catheter device (730) as illustrated in FIG. 7.

Figure 8:
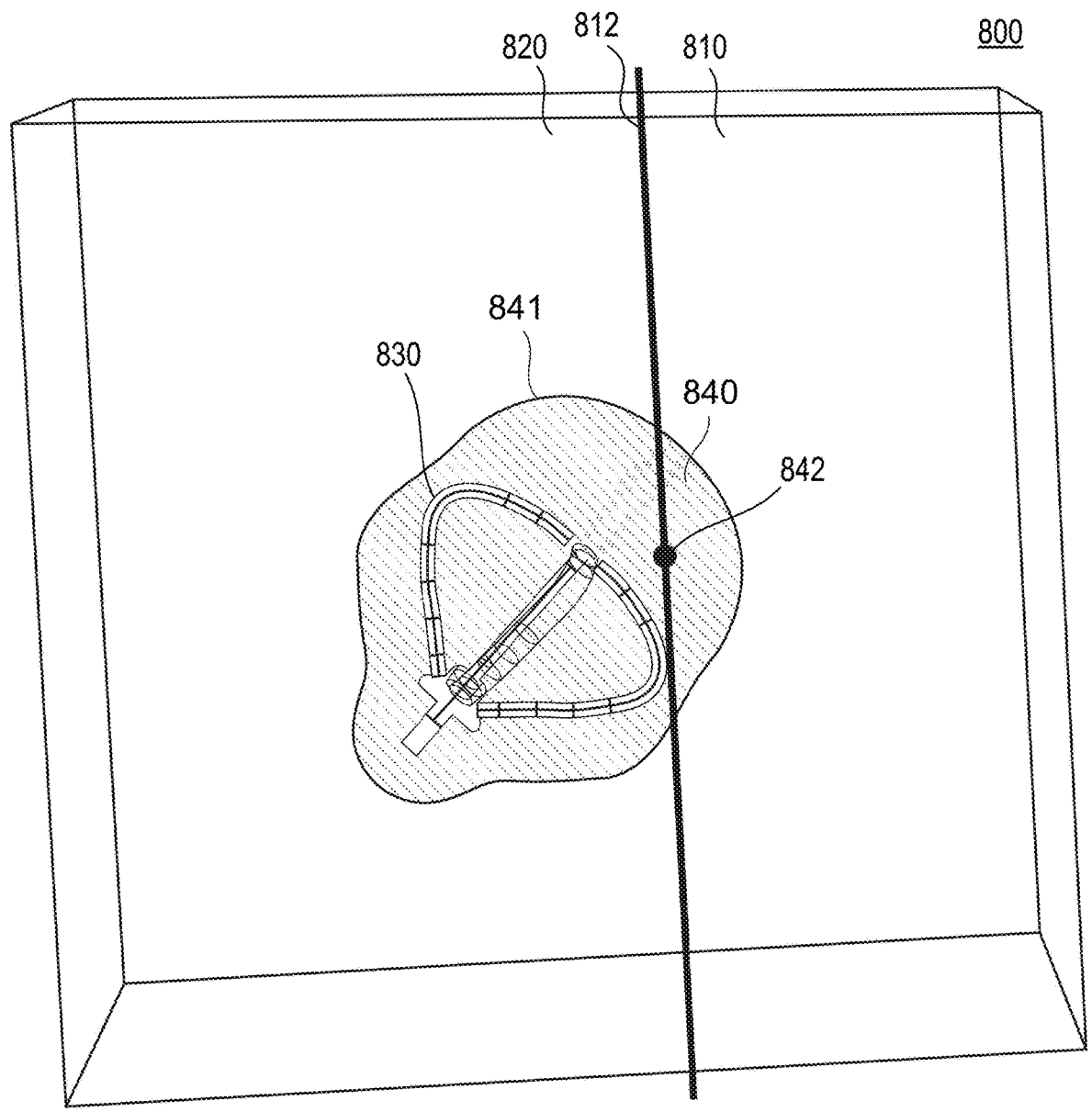
FIG. 8 is a simulated illustration of an ablation device in patient anatomy, according to embodiments.

FIG. 8 provides an illustration of an ablation device (830) in contact with a tissue region (810) and a simulated or an expected ablation zone (840) to be generated by pulsed electric field ablation. The tissue region (810) interfaces a blood pool (820) at a tissue wall surface or blood-tissue interface (812) where a catheter device (830) in the form of a partially deployed focal ablation catheter is disposed. In FIG. 8, the distal portion of the fully deployed device (830) has the form of a basket of splines and the device engages the tissue interface (812) at an oblique orientation with respect to the blood-tissue interface (812). The device (830) can be configured to generate a pulsed electric field (indicated by field contour (841)) that can produce an expected ablation zone (840) via irreversible electroporation. The ablation zone (840) is centered (or has maximal depth) at a tissue surface or interface location (812), which in this case corresponds to the location on the tissue surface closest to the distal tip of the catheter device (830) as illustrated in FIG. 8.

As shown in FIGS. 4-8, the ablation zone generated by a pulsed electric field may be centered at a tissue surface location (generally an endocardial surface of cardiac tissue abutting a blood pool) and vary with respect to the device geometry (e.g., based generally on the deployment extent of the device and/or the device orientation with respect to the local tissue interface). In some embodiments, an expected transmural ablation zone (where the ablated zone of tissue extends continuously through tissue thickness from the endocardial side to the epicardial side of the tissue) may exhibit a similar pattern.

In some embodiments, with an estimated expected shape of the ablation zone (including the approximate center of the ablation zone) and its dependence on one or both of device deployment and device orientation with respect to the local tissue wall, a representation of the ablation zone, for example a minimum expected ablation zone, may be graphically provided when a map of the tissue surface anatomy is available.

Referring back to FIG. 9A, after determining and presenting the expected ablation zone, method (900) can wait for confirmation (e.g., from a user or compute device) as to whether to deliver the ablation pulse, at (916). For example, a user can view the expected ablation zone that is presented, and determine whether the expected ablation zone is suitable for treatment or requires further adjustment. The user can provide an input (e.g., via input/output device (48, 148)) that indicates whether to proceed with ablating the tissue. Alternatively or additionally, a compute device (e.g., processor (42, 142)) can be programmed to evaluate the expected ablation zone, and depending on whether the expected ablation zone meets certain parameters (e.g., a predetermined amount of overlap with a previous ablated zone, e.g., for forming a continuous lesion), determine whether to proceed with ablating the tissue. When ablation is not to proceed (e.g., because the expected ablation zone requires adjustment and therefore further re-positioning and/or re-configuration of the ablation device is necessary), (916—No), the process may return to (904). In such cases, the ablation device can be re-positioned, at (904), and/or re-configured, at (906), and the spatial characteristics of the device re-evaluated for determining the expected ablation zone after such adjustments to the ablation device. In some embodiments, the expected ablation zone can be updated and displayed in real-time, e.g., on a tissue map of the target tissue surface. When ablation is to proceed, (916—Yes), the tissue may be ablated by the ablation device and the ablated zone presented (e.g., on the tissue map), at (918).

Figure 13:
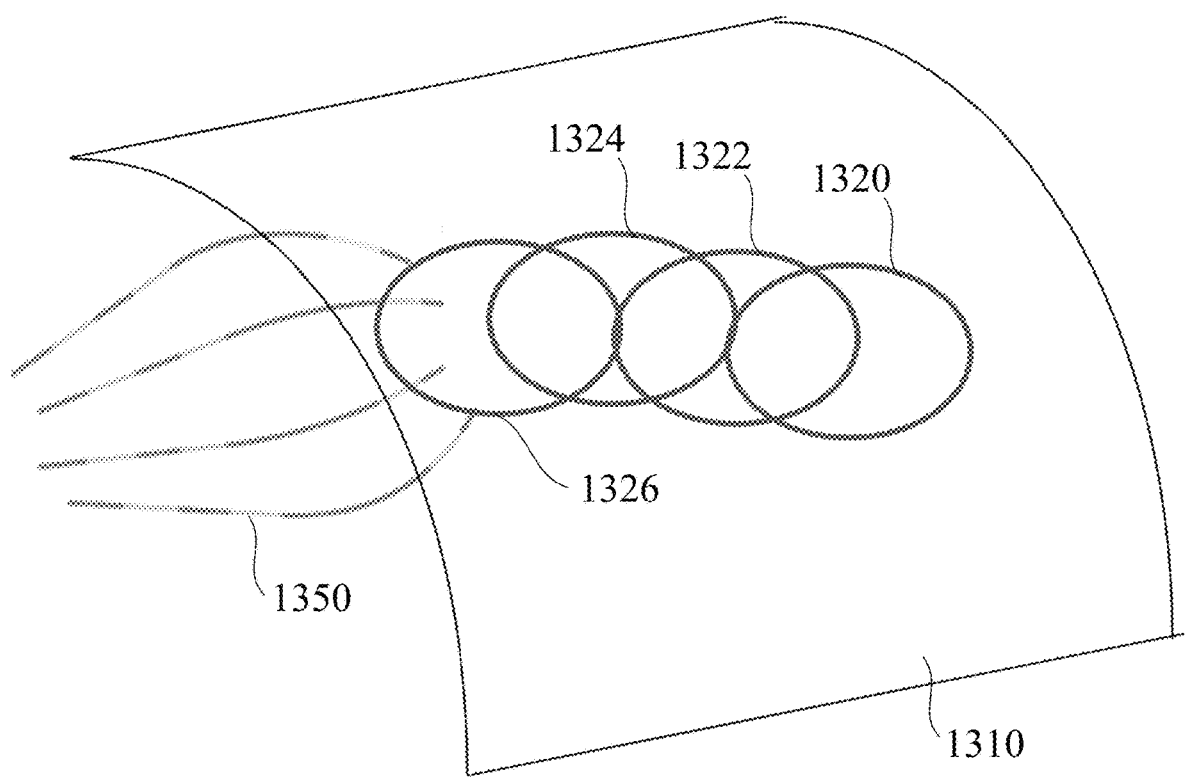
FIG. 13 is a perspective view of an anatomical surface map, according to embodiments.

In some embodiments, a mapping system (e.g., mapping system (10, 140)) separate from a signal generator (e.g., pulse waveform generator (130)) can send a signal to the signal generator to cause the signal generator to generate a pulse waveform to be delivered to the ablation device, such that the ablation device generates an electric field that produces an ablated zone corresponding to the expected ablation zone. In some embodiments, the mapping system can be integrated with a signal generator, and upon determining that ablation is to proceed, the mapping system can generate and deliver the pulse waveform to the ablation device. As described in more detail herein, FIGS. 12 and 13 depict ablation zones (1220, 1222, 1224, 1320, 1322, 1324, 1326) on a tissue surface (1210, 1310).

In some embodiments, systems, devices, and methods described herein can base the ablated zone on the expected ablation zone (e.g., have the ablated zone be the same as the expected ablated zone). Accordingly, after ablating the tissue, at (918), such systems, devices, and methods can present the ablated zone by changing the representation of the expected ablation zone to signify that the area has been ablated. For example, the expected ablation zone can be visually depicted using a first set of indicia or coloring before ablation, and the abated zone can be visually depicted using a second set of indicia or coloring different from the first set after ablation.

In some embodiments, systems, devices, and methods can use further methods to detect the tissue area that has been ablated (for example, using signals (e.g., impedances) collected by one or more sensor(s) (e.g., electrode(s) (116, 122), receiver (118)), or using an external device). In such embodiments, systems, devices, and methods can further adapt its methods (e.g., models, algorithms) for determining an expected ablation zone based on the detected ablated area. For example, analysis of the expected ablation zone and how that compared to the actual ablated area, along with parameters associated with the tissue and/or ablation device (e.g., thickness of tissue, tissue type, ablation device geometry and/or positioning, etc.) that may have caused discrepancies between the expected ablation zone and actual ablated area, can be used to improve future determinations of expected ablation zones.

When delivery of ablation pulses has not been completed by the ablation device (e.g., when using the ablation device to generate a contiguous lesion line, as further described with reference to FIG. 12), at (920—No), the process may return to (904) such that the ablation device may be navigated to another location and additional ablation pulses may be delivered. For example, when the ablation device is at a second location different from the first location the receiver may receive data representative of signals in response to the electric or magnetic field. A second position and a second orientation of the ablation device may then be determined based on the data representative of the signals. A second expected ablation zone of the ablation device in the tissue surface may be determined based on the second position and the second orientation of the ablation device.

A visual representation of the ablated zone may be displayed by the output device using a first set of indicia and a visual representative of the second expected ablation zone using a second set of indicia different from the first set of indicia. For example, FIG. 12, as further described below, illustrates a visual representation of a first set of three ablated zones (1220, 1222, 1224) represented by a first set of indicia (e.g., solid lines) and a second expected ablation zone (1230) represented by a second set of indicia (e.g., broken lines).

In some embodiments, a first ablated zone and a second ablated zone may form a portion of a continuous lesion in the tissue surface. For example, the signal generator may be activated to generate the pulse waveform to be delivered to the ablation device such that the ablation device produces a second ablated zone corresponding to the second expected ablation zone when the second expected ablation zone has an area of overlap with the ablated zone that is greater than a predetermined value. FIG. 12 illustrates a process of generating a contiguous lesion lines using the systems and devices described herein. A distal device geometry in the form of a focal ablation device (1250) is shown at an endocardial surface (1250). The estimated ablation zone (1230) for the current placement of the device is displayed on the endocardial surface (1210), in FIG. 12 as a dashed contour. In FIG. 12, previous ablated zones (1220, 1222, 1224) are illustrated by solid contours. If this placement and the expected ablation zone have adequate overlap with previous ablated zones (1220, 1222, 1224) as determined by a user, the user may ablate with the current device placement and mark the expected zone as an ablated zone, whereupon the display may update to render the dashed contour as a solid contour instead to indicate completed ablation, as depicted by ablation zone (1326) in FIG. 13. In some embodiments, various other renderings of ablated zones and expected ablation zones may be used to visually differentiate zone types, including without limitation, different and distinct colors, contours, shading, transparencies, or a variety of graphical rendering methods that render the expected ablation zones and the already ablated zones visually distinct.

This process can be continued to generate a series of overlapping ablated zones for contiguous lesion line generation. In some embodiments, the size of the depicted expected ablation zones can be illustrated to be smaller than the simulated or pre-clinically determined zone size as a method of prescribing closer placement of adjacent ablations to ensure adequate lesion overlap. Furthermore, the shape and size of the surface rendering of the ablation zone can both generally depend on device orientation with respect to the local tangent plane and/or on device deployment state.

When the ablation is completed, (920—Yes), the ablation device may be withdrawn from the cardiac chamber and the patient, at (922).

It should be understood that the examples and illustrations in this disclosure serve exemplary purposes and departures and variations such as numbers of splines, number of electrodes, and so on, or a variety of focal ablation devices such as linear ablation catheters etc. can be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

I claim:

1. An apparatus, comprising:
a memory; and
a processor operatively coupled to the memory, the processor configured to:
    activate a field generator to generate an electric or magnetic field such that signals are receivable by a receiver coupled to an ablation device disposed adjacent to a tissue surface;
    obtain processed data associated with the signals;
    determine a position and an orientation of the ablation device based on the processed data;
    display, via an output device, a map of the tissue surface, the map of the tissue surface constructed from a plurality of points that form a point cloud;
    determine a nearest distance from the ablation device to the tissue surface;
    in response to the nearest distance being less than a predefined value, identify a set of points from the plurality of points within a predefined distance from a distal end of the ablation device;
    determine a centroid of the set of points;
    determine a local tangent plane to a surface extending through the centroid;
    determine a center of an expected ablation zone based on the position and the orientation of the ablation device relative to the local tangent plane, the center representing a location of the tissue surface having a maximum depth of ablation; and
    display, via the output device, a visual representation of the expected ablation zone in the map of the tissue surface.

2. The apparatus of claim 1, wherein the expected ablation zone is a first expected ablation zone, the processor further configured to:
    in response to a change in the position or the orientation of the ablation device, determine a second expected ablation zone of the ablation device in the tissue surface; and
    display, via the output device, a visual representation of an ablated zone associated with the first expected ablation zone in the map of the tissue surface and a visual representation of the second expected ablation zone in the map of the tissue surface.

3. The apparatus of claim 2, wherein the processor is configured to display the visual representation of the ablated zone and the visual representation of the second expected ablation zone by:
    projecting the ablated zone in the map of the tissue surface using a first set of indicia; and projecting the second expected ablation zone in the map of the tissue surface using a second set of indicia different from the first set of indicia.

4. The apparatus of claim 1, wherein:
the ablation device includes a set of splines, each spline from the set of splines including a set of proximal electrodes and a set of distal electrodes such that the set of splines collectively includes a plurality of proximal electrodes and a plurality of distal electrodes, and
the processor is configured to determine the position and the orientation of the ablation device by:
determining a set of geometric parameters of the ablation device based on the processed data;
determining a configuration of the ablation device based on the set of geometric parameters; and
determining at least one of the position and the orientation of the ablation device based on the determined configuration of the ablation device and the processed data.

5. The apparatus of claim 4, wherein the processor is configured to determine the orientation of the ablation device by at least determining a longitudinal unit vector associated with the ablation device.

6. The apparatus of claim 4, wherein the processor is configured to determine the orientation of the ablation device by at least identifying a deployment configuration (1) having an associated set of geometric parameters that most closely matches the determined set of geometric parameters and (2) being from a set of deployment configurations each having an associated set of geometric parameters.

7. The apparatus of claim 6, wherein the processor is configured to identify the deployment configuration having the associated set of geometric parameters that most closely matches the determined set of geometric parameters by using a least squares procedure.

8. The apparatus of claim 1, further comprising an amplifier configured to amplify the signals received by the receiver,
the processor configured to obtain the processed data by digitizing and processing the signals amplified by the amplifier.

9. The apparatus of claim 1, wherein the processor is further configured to display, via the output device, a visual representation of the ablation device based on the position and the orientation of the ablation device.

10. The apparatus of claim 1, wherein the ablation device includes a plurality of electrodes,
the processor further configured to:
identify an electrode from the plurality of electrodes that is in contact with the tissue surface, the center of the expected ablation zone being at a location corresponding to a location of the electrode; and
identify an expected ablation zone shape from a plurality of expected ablation zone shapes based on the position and the orientation of the ablation device, the expected ablation zone having the expected ablation zone shape.

11. The apparatus of claim 1, wherein the processor is further configured to construct the map of the tissue surface based on processed data associated with signals received by the receiver when the ablation device is navigated to a plurality of locations along the tissue surface.

12. The apparatus of claim 1, wherein the predefined value is less than about 4 mm and the predefined distance is less than about 3 cm.

13. A method, comprising:
receiving, at one of a set of processors, data representative of signals received by a receiver coupled to an ablation device disposed adjacent to a tissue surface, the receiver receiving the signals in response to an electric or magnetic field being generated by a field generator;
determining, at one of the set of processors, a position and an orientation of the ablation device based on the data representative of the signals;
displaying, via an output device operatively coupled to one of the set of processors, a map of the tissue surface, the map of the tissue surface constructed from a plurality of points that form a point cloud;
determining, at one of the set of processors, a nearest distance from the ablation device to the tissue surface;
in response to the nearest distance being less than a predefined value, identifying, at one of the set of processors, a local set of points from the plurality of points that lie within a predefined distance from a distal end of the ablation device;
determining, at one of the set of processors, a local tangent plane to a surface based on the local set of points;
determining, at one of the set of processors, a center of an expected ablation zone based on the position and the orientation of the ablation device relative to the local tangent plane; and
displaying, via the output device, a visual representation of the expected ablation zone in the map of the tissue surface.

14. The method of claim 13, further comprising:
activating a signal generator to generate a pulse waveform to be delivered to the ablation device such that the ablation device produces an ablated zone corresponding to the expected ablation zone.

15. The method of claim 14, further comprising:
displaying, via the output device and upon delivery of the pulse waveform, a visual representation of the ablated zone in the map of the tissue surface distinct from the visual representation of the expected ablation zone.

16. The method of claim 15, wherein the receiving the data representative of the signals received by the receiver is when the ablation device is at a first location, the position of the ablation device is a first position of the ablation device, the orientation of the ablation device is a first orientation of the ablation device, and the expected ablation zone is a first expected ablation zone, the method further comprising:
receiving data representative of signals received by the receiver in response to the electric or magnetic field when the ablation device is at a second location different from the first location;
determining a second position and a second orientation of the ablation device based on the data representative of the signals when the ablation device is at the second location;
determining a second expected ablation zone of the ablation device in the tissue surface based on the second position and the second orientation of the ablation device; and
displaying, via the output device, a visual representation of the ablated zone using a first set of indicia and a visual representative of the second expected ablation zone using a second set of indicia different from the first set of indicia.

17. The method of claim 16, wherein the ablated zone is a first ablated zone, the method further comprising:
in response to the second expected ablation zone having a fractional overlap with the first ablated zone that is greater than a threshold value, activating the signal generator to generate the pulse waveform to be delivered to the ablation device such that the ablation device produces a second ablated zone corresponding to the second expected ablation zone, the first ablated zone and the second ablated zone forming a portion of a continuous lesion in the tissue surface.

18. The method of claim 17, wherein the threshold value is a predetermined value.

19. The method of claim 13, wherein the signals are first signals, the method further comprising:

receiving, at each location from a plurality of locations to which the ablation device is navigated, data representative of second signals received by the receiver in response to the electric or magnetic field generated by the field generator, the ablation device including a plurality of electrodes;

identifying, at each location from the plurality of locations, at least one electrode from the plurality of electrodes that is in contact with the tissue surface based on at least one of (i) the data representative of the second signals received by the receiver at that location or (ii) electrocardiogram (ECG) data recorded from the electrodes;

generating the point cloud including the plurality of points, each point from the plurality of points corresponding to a location of the at least one electrode identified at a different location from the plurality of locations; and constructing the map of the tissue surface using the point cloud.

20. The method of claim 13, wherein:

the ablation device includes a set of splines, each spline from the set of splines including a set or proximal electrodes and a set of distal electrodes such that the set of splines collectively includes a plurality of proximal electrodes and a plurality of distal electrodes, the determining the position and the orientation of the ablation device including:

determining a set of geometric parameters of the ablation device based on the received data representative of the signals;

determining a configuration of the ablation device based on the set of geometric parameters; and determining at least one of the position or the orientation of the ablation device based on the determined configuration of the ablation device and the received data representative of the signals.

21. The method of claim 13, further comprising displaying, via the output device, a visual representation of the ablation device relative to the map of the tissue surface based on the position and the orientation of the ablation device.

22. A system, comprising:

a field generator configured to generate an electric or magnetic field;

a signal generator configured to generate a pulse waveform for ablating tissue;

an output device; and a processor operatively coupled to the field generator, the signal generator, and the output device, the processor configured to:

activate the field generator to generate the electric or magnetic field such that signals are received by a receiver coupled to an ablation device disposed adjacent to a tissue surface;

obtain processed data associated with the signals;

determine a position and an orientation of the ablation device based on the processed data;

cause the output device to display a map of the tissue surface, the map of the tissue surface constructed from a plurality of points that form a point cloud;

determine a nearest distance from the ablation device to the tissue surface;

in response to the nearest distance being less than a predefined value, identify a local set of points from the plurality of points that lie within a predefined distance from a distal end of the ablation device;

determine a local tangent plane to a surface based on the local set of points; and determine a center of an expected ablation zone based on the position and the orientation of the ablation device relative to the local tangent plane;

cause the output device to display a visual representation of the expected ablation zone in the map of the tissue surface; and in response to the expected ablation zone corresponding to a desired ablation zone, activate the signal generator to generate the pulse waveform to be delivered to the ablation device such that the ablation device produces an ablated zone corresponding to the expected ablation zone.

23. The system of claim 22, wherein the field generator includes a set of electrode patches that generate one or more electric fields, the electric or magnetic field including the one or more electric fields generated by the set of electrode patches.

24. The system of claim 22, wherein the field generator includes a set of transmitter coils that each generates a time-varying magnetic field, the electric or magnetic field including the time-varying magnetic fields generated by the set of transmitter coils.

25. The system of claim 22, wherein the processor is further configured to:

in response to activating the signal generator, cause the output device to change the visual representation of the expected ablation zone to indicate that the expected ablation zone is ablated.

26. The system of claim 22, wherein:

the ablation device includes a set of splines, each spline from the set of splines including a set or proximal electrodes and a set of distal electrodes such that the set of splines collectively includes a plurality of proximal electrodes and a plurality of distal electrodes, and the processor is configured to determine the position and the orientation of the ablation device by:

determining a set of geometric parameters of the ablation device based on the processed data;

determining a configuration of the ablation device based on the set of geometric parameters; and determining at least one of the position or the orientation of the ablation device based on the determined configuration of the ablation device and the processed data.

* * * * *